United States Patent
Cohn et al.

(10) Patent No.: US 9,200,109 B2
(45) Date of Patent: Dec. 1, 2015

(54) BIODEGRADABLE ADHESIVE COMPOSITIONS

(75) Inventors: Daniel Cohn, Jerusalem (IL); Peter Siman, Eilaboun (IL)

(73) Assignee: YISSUM RESEARCH DEVELOPMENT COMPANY OF THE HEBREW UNIVERSITY OF JERUSALEM, LTD., Jerusalem (IL)

( * ) Notice: Subject to any disclaimer, the term of this patent is extended or adjusted under 35 U.S.C. 154(b) by 0 days.

(21) Appl. No.: 12/737,920

(22) PCT Filed: Sep. 6, 2009

(86) PCT No.: PCT/IL2009/000865
§ 371 (c)(1),
(2), (4) Date: Jul. 13, 2011

(87) PCT Pub. No.: WO2010/026590
PCT Pub. Date: Mar. 11, 2010

(65) Prior Publication Data
US 2011/0269870 A1    Nov. 3, 2011

Related U.S. Application Data

(60) Provisional application No. 61/094,329, filed on Sep. 4, 2008.

(51) Int. Cl.
*C08G 18/81* (2006.01)
*A61L 24/00* (2006.01)
*A61L 24/06* (2006.01)

(52) U.S. Cl.
CPC ......... *C08G 18/8175* (2013.01); *A61L 24/0042* (2013.01); *A61L 24/06* (2013.01)

(58) Field of Classification Search
CPC ........................................................ A61L 24/06
USPC ............ 523/118; 526/269, 298; 606/908, 910
See application file for complete search history.

(56) References Cited

U.S. PATENT DOCUMENTS

| 4,440,910 A | 4/1984 | O'Connor | |
|---|---|---|---|
| 5,626,863 A | 5/1997 | Hubbell et al. | |
| 6,103,778 A * | 8/2000 | Hyon et al. | 523/111 |
| 6,699,940 B2 * | 3/2004 | Shalaby | 525/308 |
| 7,138,441 B1 | 11/2006 | Zhang | |
| 2002/0026005 A1 * | 2/2002 | Munro | 524/514 |

FOREIGN PATENT DOCUMENTS

EP    0 952 171    10/1999

OTHER PUBLICATIONS

International Search Report for PCT/IL2009/000865, mailed Aug. 20, 2010.
Hiemenz, "Polymer Chemistry, The Basic Concepts", Marcel Dekker, Inc, New York, NY, 1984, pp. 423, 431 and 432.

* cited by examiner

*Primary Examiner* — Tae H Yoon
(74) *Attorney, Agent, or Firm* — Nixon & Vanderhye P.C.

(57) ABSTRACT

The present invention provides a polymerizable adhesive composition comprising: (i) at least one cyanoacrylate monomer; and (ii) at least one polymerizable compound containing (a) one or more polymerizable carbon-carbon double bonds and (b) one or more biodegradable (BDG) chains. Further are provided the copolymerization product of this composition, and uses thereof in biomedical applications.

18 Claims, 3 Drawing Sheets

TMP{([LA]$_8$[CA]$_2$[LA]$_8$)-MA}$_3$

PEG600{([LA]₈[CL]₂[LA]₂[CL]₂[LA]₈[CL]₂[LA]₈)-MA}₂

BIODEGRADABLE ADHESIVE COMPOSITIONS

This application is the U.S. national phase of International Application No. PCT/IL2009/000865 filed 6 Sep. 2009, which designated the U.S. and claims priority to U.S. Application No. 61/094,329, filed 4 Sep. 2008, the entire contents of each of which are hereby incorporated by reference.

There is a wide variety of materials which are foreign to the human body and which are used in direct contact with its organs, tissues and fluids. These materials are called Biomaterials, and among them, polymers play a pivotal role.

Tissue adhesives are being used in a diversity of biomedical applications to attach tissues temporarily, until healing is completed. In the surgical arena, adhering, rather than suturing or stapling planes of tissues, has several highly attractive features, provided it is fast-acting and assures complete closure and adhesive efficiency for the time required. A tissue adhesive must be biocompatible and is required to degrade within approximately the same time interval as the healing process. In addition, it has to ensure a union capable of bearing the physiological load for the time required, connect quickly to tissues, be easy to apply and affordable.

The diverse uses of tissue adhesives and sealants can be exemplified by their utilization in craniofacial and facial plastic surgery, in the joining of topical skin cuts, in adhering the cornea during cataract surgery and in various gynecological applications. These materials perform also as sealants in various areas such as to prevent air leaks after pulmonary resection and to stop fluid oozing following brain surgery.

Among the existing adhesives in clinical use, only few meet these attributes, albeit to a limited extent. They include alkyl cyanoacrylates and natural sealants such as collagen and fibrin. Since most natural glues show substantially lower adhesive as well as cohesive strength, compared to their synthetic counterparts, natural glues are rarely used as tissue adhesives, but as sealants. Furthermore, since fibrin glues are manufactured from human blood or plasma, the menace of the transmission of infective agents cannot be completely ruled out.

Cyanoacrylates (CA), on the other hand, have the following advantages: They have high adhesive as well as cohesive strength, they are faster to apply and less painful than sutures and they typically give good esthetic results.

However, the clinical use of alkyl cyanoacrylates has many disadvantages, and is therefore largely limited, due to their:
high toxicity and possibility of tissue damage and impairment of function, which prohibits the use of cyanoacrylates on internal organs and limits their use to a topical skin use. This is due to the fact that [i] CA acts as an organic solvent inside the body; [ii] PCA's very high stiffness and [iii] the formation of formaldehyde as a degradation product.
high rigidity and glassiness (are felt as a piece of glass by the patient) of the PCA formed, which makes the adhesive painful.
excessively low viscosity, which makes them difficult to apply
difficulty in controlling the adhesion rate: once the polymerization process has started, it cannot be stopped and, therefore, the surgeon has little latitude to rectify errors made during the application of the adhesive
high heat of polymerization (exothermic reaction), which may cause thermal damage to tissues, especially if the layer spread is too thick
difficulty in controlling the degradation rate: it is not possible to tailor-make the adhesive to have a pre-determined degradation time.

One approach has been to change the cyanoacrylate monomer. This resulted in some commercial products, such as Dermabond, Histoacryl, PeriAcryl and Omnex. However, the impact of these modifications is limited and, therefore, they very much retain the drawbacks of CAs.

In another attempt to overcome the known problems of commercial cyanoacrylates while retaining their adhesive properties, WO 00/72761 (to Zhang) discloses blends of commercially available cyanoacrylate (CA) adhesives and biodegradable (BDG) polymers or copolymers, composed of different degradable monomers. In this case, the BDGs, such as lactide-epsilon-caprolactone copolymers, were added as thickeners of the CA monomer and plasticizers of the resultant PCA polymers, but these BDGs are not easily biodegradable and do not easily dissolve into CA at the required concentrations, therefore largely limiting their applicability. Furthermore, the fact that these are only physical mixtures of two polymers, namely, the PCA adhesives and the BDG polymers, the latter degrade, leaving behind the PCA, with it shortcomings, such as its stiffness, rate of degradation and toxicity.

U.S. Pat. No. 6,224,622 (to Kotzev) suggests to compatibilize the lactide-epsilon-caprolactone copolymers (and similar BDGs) used as thickeners by Zhang, by incorporating into the copolymer some CA segments. These CA-containing copolymers are synthesized at high temperatures in the laboratory (around 165° C.), and are non-adhesive by themselves since the CA units within these copolymers are fully polymerized, and are then dissolved in the CA adhesive, as thickeners and plasticizers, to obtain, once again, blends of CAs and BDG/CA copolymers. Once again, when the BDG polymers degrade, they leave behind the PCA, with it shortcomings, such as its stiffness, rate of degradation and toxicity.

U.S. Pat. No. 6,699,940 (to Shalaby) discloses CA based adhesives comprising CA-capped heterochain polymers, such as those comprising one or more oxyalkylene, alkylene carbonate and ester derivatives of cyclic lactones, whereas these adhesives form a PLA having on each end a CA monomer. Thus, while solving the viscosity issue, these polymers have a relatively low CA content, since the CA units are only incorporated at the end of the large heteroatom component, and will therefore have a relatively low adhesiveness. Shortening the heteroatom component, enabling the incorporation of additional. CA units, will increase the adhesiveness, but at the expense of increased stiffness, a higher polymerization exotherm and also a higher toxicity due to the formaldehyde produced by the degradation of the PCA Thus, there is an on-going need to develop novel adhesives which would overcome the drawbacks of commercial cyanoacrylates and blends thereof, while maintaining adequate adhesiveness. Preferably, such adhesives would have controlled biodegradability, controlled polymerization (curing) rate, be easy, safe and comfortable to apply in vivo, and would generally be versatile and programmable, depending on the exact application and needs.

The present inventors have now found that CA can be copolymerized in situ, with a compound containing at least one polymerizable double bond and at least one BDG chain, to obtain a copolymer composed of cyanocrylate-derived units and BDG chains. The copolymerization, accomplished under physiological conditions, via the double bonds (present both in the CA monomers and in the polymerizable compounds) provides adhesives with the desired properties.

Accordingly, the present invention relates to a polymerizable adhesive composition comprising: (i) at least one cyanoacrylate monomer; and (ii) at least one polymerizable compound containing (a) one or more polymerizable carbon-carbon double bonds and (b) one or more biodegradable (BDG) chains.

Even more preferably these BDG chains comprise also additional moieties to impart to the product additional advantageous features such as enhanced flexibility and higher cohesive strength.

The term "polymerizable compound" as used herein, generally refers to a chemical compound, substituent or moiety capable of undergoing a self-polymerization and/or co-polymerization reaction under physiological conditions. In particular this refers to a compound having a polymerizable double bond, which is capable of undergoing polymerization via its double bond.

The term "polymerizable composition" refers to a mixture of at least one CA monomer, at least one polymerizable compound containing the one or more polymerizable carbon-carbon double bonds and the one or more biodegradable (BDG) chains, and any additional ingredients added to promote in situ polymerization or inhibit premature polymerization.

It has been found by the present inventors that adhesive polymerizable compositions can be prepared by using less than 50% by weight of the cyanoacrylate monomer(s) from the total weight of the cyanoacrylate monomer(s) and the polymerizable compounds.

Even more so, acceptable polymerizable compositions can be prepared by using less than 40%, less than 30%, less than 20% and even less than 10% by weight of the cyanoacrylate monomer(s), from the total weight of the cyanoacrylate monomer(s) and the polymerizable compounds combined together, depending on the exact application or need, while overcoming the disadvantages associated with high ratios and amounts of CA, in particular:

This has several advantages, among which are:

a) lowering the toxicity of the obtained polymeric adhesive, which is correlated to the amount of CA units, since toxic formaldehyde is a product of the degradation of PCA under physiological conditions;

b) minimizing the painful "feel" of the PCA products, under physiological conditions, by lowering their stiffness by suitably copolymering CA monomers with the polymerizable compounds of the present invention;

c) fine-tuning the rate of degradation by tailoring the BDG chain and the ratio between the CA units and the BDG-containing polymerizable compounds. Choosing the polymerizable compound to have biodegradable chains therein enables obtaining bioadhesive polymers having controllable degradability under physiological conditions. The rate of degradation can be further controlled by controlling the hydrophilicity of the polymerizable composition (final mixture).

d) lowering drastically the increase in temperature at the site, due to the exothermic nature of the polymerization, by the copolymerization of CA with the polymerizable compounds of the present invention, such as those having large BDG chains. The copolymer has less CA units, having instead bulky "equivalents" to the CA. Thus, for a given quantity (weight) of monomers, less polymerizable C=C bonds will be present in the polymers of the present invention, and therefore, the polymerization of the monomers present in said given amount of monomers will reach lower temperatures.

The term "cyanoacrylate monomer" refers to any polymerizable cyanoacrylate, preferably selected from the group consisting of alkyl 2-cyanoacrylate, alkenyl 2-cyanoacrylate, alkoxyalkyl 2-cyanoacrylate, and carbalkoxyalkyl 2-cyanoacrylate, wherein the alkyl group of said one or more cyanoacrylates has 1 to 16 carbon atoms.

More preferably, the cyanoacrylate monomer is selected from the group consisting of methyl 2-cyanoacrylate, ethyl 2-cyanoacrylate, n-propyl 2-cyanoacrylate, iso-propyl 2-cyanoacrylate, n-butyl 2-cyanoacrylate, iso-butyl 2-cyanoacrylate, hexyl 2-cyanoacrylate, n-octyl 2-cyanoacrylate, 2-octyl 2-cyanoacrylate, 2-methoxyethyl 2-cyanoacrylate, 2-ethoxyethyl 2-cyanoacrylate and 2-propoxyethyl 2-cyanoacrylate.

Yet more preferably, the cyanoacrylates of this invention are ethyl cyanoacrylate, butyl cyanoacrylate, hexyl cyanoacrylate, octyl cyanoacrylate and ethylhexyl cyanoacrylate The polymerizable compounds of the present invention, which are operable according to the invention, are prepared via a pre-monomer compound, which is prepared following any suitable synthetic pathway including, for example, condensation reactions, ring-opening reactions, and similar reactions, this pre-monomer compound being modified to incorporate therein a polymerizable carbon-carbon double bond functionality, such that the resulting compound may be suitably used in subsequent polymerization reactions via the polymerizable carbon-carbon double bond incorporated therein. This one or more polymerizable carbon-carbon double bond can be incorporated into the pre-monomer compounds at any stage of the synthetic process whereby said pre-monomer compounds or precursors are prepared.

For the purpose of the present invention, the term "pre-monomer" describes the precursor of the polymerizable compound of the present invention, before the addition of the polymerizable double bond to it.

In view of the above, it is understood that the polymerizable compounds of the invention are either non-polymeric, monomeric, oligomeric or polymeric. Thus, this term also refers to polymers, copolymers and mixtures thereof, as long as they have at least one polymerizable double bond which can copolymerize with the CA monomers under in situ The term "telechelic" is known in the art to describe low molecular weight polymers or oligomers, having two or more functional end groups. In the present case, the two functional groups are a polymerizable carbon-carbon double bond, and an additional group that can be attached to the BDG chain.

Thus, the polymerizable compound of the present invention may be described as a "telechelic oligomer" or as a "telechelic polymer".

As used herein, the terms "telechelic", "telechelic oligomer" and "telechelic polymer", all refer to an oligomers or polymer capable of entering into further polymerization via its reactive carbon-carbon double bond.

As used herein, the term "oligomer" is used to refer to a unit comprising a chain of two or more linked monomers. While this term includes a plurality of monomers of any length, more specifically it refers to a chain containing from 2 to 100 monomers, more particularly between 2 to 50 monomers.

The term "biodegradable chain" is used interchangeably with the term "biodegradable polymer", "biodegradable segment" and "biodegradable moiety" or "BDG", and includes oligomers and polymers capable of degrading in vivo at a predetermined rate.

The term "biodegradable" is known in the art and includes polymers, compositions and formulations, such as those described herein, that are intended to degrade during in vivo use.

In general, biodegradability involves the degradation of the biodegradable polymer into its component subunits, or digestion, e.g., by a biochemical process, of the polymer into smaller subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation, as defined herein, may involve cleavage of a bond (whether covalent or otherwise) internal to side-chain or that connects a side chain to the polymer backbone. For example, a therapeutic agent or other chemical moiety attached as a side chain to the polymer backbone may be released by biodegradation. In certain embodiments, one or the other or both general types of biodegradation may occur during use of a polymer. As used herein, the term "biodegradation" encompasses both general types of biodegradation.

The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, typically, the greater the molecular weight of a semi-crystalline polymer, the higher its degree of crystallinity, and its biodegradation is usually slower. The term "biodegradable" is intended to cover materials and processes also termed "bioerodible, "bioabsorbable" and "bioresorbable".

In certain embodiments wherein the biodegradable polymer also has a therapeutic agent or other material associated with it, the biodegradation rate of such polymer may be characterized by a release rate of such materials. In such circumstances, the biodegradation rate may depend on not only the chemical identity and physical characteristics of the polymer, but also on the identity of material(s) incorporated therein.

In certain embodiments, polymeric formulations of the present invention biodegrade within a period that is acceptable for the desired application.

In certain embodiments, such as in vivo therapy, such degradation occurs in a period usually less than about five years, one year, six months, three months, one month, fifteen days, five days, three days, or even one day of exposure to a physiological environment, also termed "physiological conditions", with a pH between 1.5 and 9, preferably between and 8 having a temperature of between 25 and 45° C., preferably between 30 and 40° C., and more preferably between 36° C. and 39° C.

In other embodiments, the polymer degrades in a period of between about one hour and several weeks, depending on the desired application of the biodegradable polymer.

In order to choose a suitable BDG chain, the required biodegradability rate range should be determined (minutes, hours, days, weeks or months). Then, the biodegradability of the selected compound can be evaluated in a certain time frame.

For example, for a large number of applications, including in the present application, the polymer polycyanoacrylate (PCA) is considered essentially non-biodegradable, although it will, in fact, biodegrade, albeit very slowly, over time, so slow that if used as a bioadhesive, in some instances it may actually hamper the healing process.

Preferably, the one or more BDG chains in the polymerizable compound (ii) chain is composed of repeating units having the structure of ring-opened forms of one or more aliphatic esters, carbonates or anhydrides Preferably, the one or more BDG chains in the polymerizable compound (ii) chain is composed of repeating units having the structure of ring-opened forms of one or more cyclic esters.

In particular, the building blocks of the one or more BDG chains in compound (ii) are selected from hydroxy carboxylic acid units or their respective lactones, lactic acid, lactide, ε-caprolactone, glycolic acid, glycolide, β-propiolactone, δ-glutarolactone, δ-valerolactone, β-butyrolactone, ethylene carbonate, trimethylene carbonate, γ-pivalactone, α,α-diethylpropiolactone, p-dioxanone, 1,4-dioxepan-2-one, 3-methyl-1,4 dioxanone-2,5-dione, 3,3-dimethyl-1,4-dioxanone-2,5-dione, cyclic esters of α-hydroxybutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-a-methylvaleric acid, α-hydroxypentanoic acid, α-hydroxystearic acid, α-hydroxylignoceric acid, salycilic acid, amino carboxylic units and any mixtures thereof.

In particular, the building blocks of the one or more BDG chains in compound (ii) are cyclic esters selected from the group consisting of (dl)lactide, (l)lactide, ε-caprolactone, glycolide, dioxanone, lactones and trimethylene carbonate.

According to a preferred embodiment of the present invention, the BDG chain is composed of repeating units obtained from ring-opening polymerization of lactide and of ε-caprolactone.

Various structures constructed by these units are named throughout this application by using the "CL", "LA" terms, referring to caprolactone and lactic acid, respectively.

As will be explained in detail hereinbelow, when the polymerizable compounds contain two or more polymerizable double bonds, the product formed from the copolymerization of the cyanoacrylate monomer and the polymerizable compounds of the invention, has an enhanced biodegradability, since in this case, the BDG chains can form part of the polymeric backbone, and hence—when the BDG chains biodegrade, the polymer backbone is cleaved.

Thus, according to a preferred embodiment of the present invention, compound (ii) contains two or more BDG chains each terminated with an end group containing a polymerizable carbon-carbon double bond.

Preferably, these two or more BDG chains are linked to a single multifunctional moiety.

As can be seen in the examples section which follows, the acrylate group constitutes an easy source of a polymerizable double bond.

Therefore, according to a preferred embodiment of the present invention, each of the two or more BDG chains is terminated with an end group which is an acrylate group or a methacrylate group.

The term "acrylate" shall be understood herein to refer to an acrylate moiety and/or a methacrylate moiety.

Acrylates that can be used to introduce the polymerizable double bond functionality into the polymerizable compound of the present invention are one or more mono-, di-, tri-, tetra- and/or higher functionality acrylates, which have in addition to the carbon-carbon double bond, a group that can link to the BDG chain, this group being a hydroxy group (hydroxyacrylates), an amine group, a thiol group etc.

Examples of hydroxyacrylates or hydroxymethacrylates, include, but are not limited to, butanediol monoacrylate (BDMA), 2-hydroxyethyl acrylate (HEA), hydroxyethyl methacrylate (HEMA), 2-hydroxypropyl acrylate (HPA), hydroxypropyl methacrylate (HPMA), polycaprolactone modified hydroxyethyl hexylacrylate, hydroxybutyl acrylate, hydroxybutyl methacrylate, polyethylene glycol monoacrylate, polyethylene glycol monomethacrylate, glycerol diacrylate, glycerol dimethacrylate, trimethylolpropane diacrylate, trimethylolpropane dimethacrylate, pentaerythritol triacrylate, pentaerythritol trimethacrylate, dipentaerythritol pentaacrylate, dipentaerythritol pentalnethacrylate, the acrylate of phenyl glycidyl ether, the methacrylate of phenyl glycidyl ether, and combinations comprising at least one of the foregoing acrylates.

Preferable acrylates according to the present invention include hydroxyethylacrylate (HEA), Hydroxy ethyl methacrylate (HEMA), Hydroxy propyl methacrylate (HPMA), acrylic acid, and amine- and SH-containing C=C-containing monomers.

It has been found by the present inventors that the structures of the polymerizable compounds of the present invention, can be defined as a compound having at least one polymerizable double bond, and containing a moiety H having the formula:

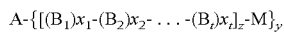

wherein:
a) A is a component having a functionality ≥1, selected from water, hydroxyl, amine, thiol, aldehyde, isocyanate (NCO), acyl chloride, carboxylic acid-terminated segments, a molecule containing a reactive unsaturated bond;
b) $x_1, x_2, \ldots, x_n$ are the number of the $(B_1), (B_2), \ldots (B_n)$ components, respectively, being ≥0;
c) B is a component selected from the group consisting of aliphatic esters, amides, urethanes, components having a polymerizable double bond, carbonates or anhydride groups, provided that at least one of $(B_1), (B_2), \ldots (B_n)$ is biodegradable;
d) z is the number of times a $[(B_1)x_1-(B_2)x_2-\ldots-(B_n)x_n]$ component repeats itself along a specific chain, being ≥1;
e) y is the number of $\{[(B_1)x_1-(B_2)x_2-\ldots-(B_n)x_n]_z-M\}$ blocks connected to A and is ≥1;
f) w is the functionality of the A component and is ≥1 and <y;
g) M is an end group able to react with the F group of V, as defined herein, preferably being selected from hydroxyl, amine or carboxylic acid moieties;

In particular, it has been found by the inventors that compound ii can be structurally represented by the formula F3, Formula F3

Wherein BDG is a biodegradable chain, as defined hereinabove,
V= is an end group covalently attached to the BDG chain, this group providing the polymerizable carbon-carbon double bond.

A preferable functional group containing a polymerizable carbon-carbon double bond includes, for example, an acrylate group, a (metha)acryloyl group, an allyl group, a vinyl group, a (meth)acrylamido group, a vinyloxy group and an acetylenic group.

Preferably, V= is an acrylate group or a methacrylate group, as it has been defined hereinabove.

According to another preferred embodiment of the present invention, V= is a vinyl moiety or an olefinic moiety.

MF is a monofunctional or multifunctional moiety which is linked to one or more BDG chains.

In particular, MF can be said to have a functionality of n, n being any number equal to or large than 1, but preferably being between 2 and 20, more preferably between 2 and 10, and yet more preferably between 2 and 5. Thus, the MF moiety having the n functionality is linked to n BDG chains, either the same or different, via n groups located on this MF moiety. These groups can be independently selected from water, hydroxyl, amine, thiol, aldehyde, isocyanate (NCO), acyl chloride, carboxylic acid-terminated segments, amines, thiols, alcohols, a molecule containing a reactive unsaturated bond.

For example, when n is 1 MF is selected from water, methanol, ethanol, polyethylene glycol monomethylethers, polypropylene glycol monomethylethers, ethyl amine, butyl amine, polyoxoethylene amine monomethylethers, polypropylene amine monomethylethers, acetic acid, propionic acid, acrylic acid, acetoyl chloride, polyoxoethylene monocarboxylic acid, polypropylene monocarboxylic acid monomethylethers, biologically active molecules, and any combinations thereof.

When n is 2, MF is selected from ethylene glycol, propylene glycol, polyethylene glycol, polypropylene glycol, polycaprolactone diol, polyethylene glycol-polypropylene glycol-polyethylene glycol triblocks, ethane diamine, butane diamine, ethanol amine, polyoxoethylene diamine, polyoxopropylene diamine, hydroxyethyl methacrylate, hydroxypropyl acrylate, aminoethyl methacrylate, oxalic acid, adipic acid, maleic acid, fumaric acid, itaconic acid polycaprolactone dicarboxylic acid, polyoxoethylene dicarboxylic acid, polytetramethylene glycol, lactic acid, glycolic acid, hydroxybutyric acid, polyesters such as polylactic acid, polyglycolic acid or polycaprolactone, polyamides or Polyanhydrides, amino acids, biologically active molecules, and any combinations thereof.

Wherein n is 3, MF is selected from trimethylolpropane, ethoxylated trimethylolpropane, glycerol, polyoxoethylene triamine, polyoxopropylene triamine, citric acid, tartaric acid, oligopeptides, biologically active molecules, oligohydroxy ethylmethacrylate, oligovinyl alcohol, oligoacrylic acid, oligoethyleneglycol methacrylate and combinations thereof.

In particular, MF is selected from an acrylate derivative, a polyethylene glycol, a polypropylene glycol, trimethylolpropane (TMP) and ethoxylated trimethylolpropane (TMPO).

Exemplary preferable MF groups include ethylene glycol, propylene glycol, polyethylene glycol, polypropylene glycol, polycaprolactone diol, polyethylene glycol-polypropylene glycol-polyethylene glycol triblocks, ethane diamine, butane diamine, ethanol amine, polyoxoethylene diamine, polyoxopropylene diamine, oxalic acid, adipic acid, maleic acid, fumaric acid, itaconic acid, polycaprolactone dicarboxylic acid, polyoxoethylene dicarboxylic acid, polytetramethylene glycol, lactic acid, glycolic acid, hydroxybutyric acid, polyesters such as polylactic acid, polyglycolic acid or polycaprolactone, polyamides or polyanhydrides, trimethylolpropane, ethoxylated trimethylolpropane, glycerol, polyoxoethylene triamine, polyoxopropylene triamine, citric acid, tartaric acid, oligopeptides, biologically active compounds, oligohydroxy ethylmethacrylate, oligovinyl alcohol or oligoacrylic acid.

Thus, MF is linked to the BDG chains via one or more of an ester bond, a carbonate bond, an anhydride bond, an amide bond, a thioester bond, an urea bond or an urethane bond, as determined by the various routes of preparation of the polymerizable compounds of the invention, described in detail hereinbelow.

In many cases, it has been found that MF is a polyol.

The term "polyol" refers to a molecule which has at least two or more functional hydroxyl groups and is linked to the BDG chains via one or more of an ester bond.

Examples of polyols include but are not limited to diols, triols, and macromers such as macrodiols. Preferably the polyol has a molecular weight of 200-5000, more preferably 200-2000, and even more preferably 200-1000.

According to a preferred embodiment of the present invention, MF is a diol or a triol. Even more preferably the diol is polyethylene glycol (PEG) or polypropylene glycol (PPG), and the triol is trimethylol propane (TMP) or a derivative thereof, such as ethoxylated trimethylolpropane (TMPO).

As can be seen in the examples and schemes below, MF may also be a diisocyanate linked to the BDG chains via an urethane bond.

Following the definition of polymerizable compound ii as a telechelic oligomer or polymer, and given the detailed description of the structure of polymerizable compounds of the present invention, as given above, it can be understood by a person skilled in the art that the present invention also provides a telechelic polymer comprising two or more biodegradable chains composed of units having the structure of ring-opened forms of one or more cyclic esters, wherein said biodegradable chains are terminated with reactive end groups containing carbon-carbon double bond.

According to a preferred embodiment of the present invention, there is provided a triblock copolymer, having a central polyether block and two lateral biodegradable blocks composed of units having the structure of ring-opened forms of one or more cyclic esters selected from the group consisting of (dl)lactide, (l)lactide, ε-caprolactone, glycolide, dioxanone, lactones and trymethylene carbonate.

Preferably, the central block is polyethylene glycol or polypropylene glycol, the biodegradable blocks are composed of the ring-opened form of lactic acid and ε-caprolactone and the end groups are acrylate groups. Additional central blocks can be polytetramethylene glycol and polycaprolactone.

Further preferably, in this telechelic polymer, the two or more biodegradable chains are linked to a single multifunctional moiety selected from the group consisting of diol, triol and diisocyante through the hydroxyl or isocyanate groups of said multifunctional moiety.

In one embodiment the polymerizable compound(s) consist, partially or totally, of materials that, once polymerized and/or crosslinked become stiffer, as required. This process may be due to the polymerization and/or crosslinking reaction and also due to crystallization phenomena that may take place, following different kinetics, depending on the composition, crystallizability as well as % present of the polymerizable compound(s).

Since the polymerizable compositions of the present invention may be kept in this state for long periods of time before the actual use thereof, they should preferably contain an inhibitor of anionic and/or radical polymerization to prevent premature polymerization of the composition and spoiling thereof.

The term "polymerization inhibitor" refers to conventional acid polymerization inhibitors and free radical inhibitors of cyanoacrylate esters including materials such as acid polymerization inhibitors including sulfur dioxide, glacial acetic acid, and the like, and free radical polymerization inhibitors such as hydroquinone, 4-methoxyphenol and the like.

Because of its compatibility with topical skin applications, and the possible in situ application, the acid polymerization inhibitor is preferably sulfur dioxide which is preferably employed at from about 50 to 1000 ppm, more preferably from about 50 to 500 ppm and even more preferably 200 to 500 ppm, based on the total weight of the composition. Other preferred acid polymerization inhibitors include glacial acetic acid and other organic acids (e.g., C 2 to C 6 organic acids), and phosphoric, carboxylic and organic sulphonic acids.

Preferred free radical inhibitors include hydroquinone which is preferably employed at from about 50 to 250 ppm. Other free radical inhibitors include hydroquinone monomethyl ether, hindered phenols such as 4-methoxyphenol, 2,6-di-tert-butylphenol, t-butyl catechol, hydroxyanisole, butylated hydroxyanisole, butylated hydroxytoluene and the like.

Mixtures of free radical polymerization inhibitors and acid polymerization inhibitors are often used.

Preferably, the inhibitor is hydroquinone and is added in an amount ranging from about 0.1% to about 5% relative to the monomers present. More preferably, the inhibitor is added in an amount of about 2%.

Yet further, the polymerizable composition may contain a polymerization initiator and/or a polymerization accelerator.

The term "polymerization accelerator" as used herein means an additive for accelerating the polymerization reaction. Examples of it include polymerization initiators and transition metal catalysts.

The term "polymerization initiator" covers all compounds which are added to the polymerizable composition to initiate the polymerization and includes both a single compound or a combination of compounds.

Suitable initiators for the purpose of the present invention are those initiators which can be effective in situ, and which are not harmful in internal use.

Exemplary suitable initiators include, but are not limited to azoisobutyronitrile (AIBN), benzoyl peroxide, dicumyl peroxide, methyl ethyl ketone peroxide and lauryl peroxide.

Preferably, the initiator is benzoyl peroxide.

Additional possible initiators, depending on the application and conditions are: cyclohexanone peroxide, t-butyl hydroperoxide, t-butyl benzene hydroperoxide, t-butyl peroctoate, 2,5-dimethylhexane-2,5-dihydroperoxide, 2,5-dimethyl-2,5-di(t-butylperoxy)-hex-3-yne, di-t-butylperoxide, t-butylcumyl peroxide, α,α-bis(t-butylperoxy-m-isopropyl)benzene, 2,5-dimethyl-2,5-di(t-butylperoxy)hexane, dicumyl peroxide, di(t-butylperoxy isophthalate, t-butylperoxybenzoate, 2,2-bis(t-butylperoxy)butane, 2,2-bis(t-butylperoxy)octane, 2,5-dimethyl-2,5-di(benzoylperoxy)hexane, di(trimethylsilyl)peroxide, trimethylsilylphenyltriphenylsilyl peroxide, 2,3-dimethyl-2,3-diphenylbutane, 2,3-trimethylsilyloxy-2,3-diphenylbutane, and the like, and mixtures thereof.

The initiator is added in an amount ranging from about 0.1% to about 5% relative to the total weight of the monomers. Preferably, the initiator is added in an amount of about 2%.

The term "polymerization catalyst" as used herein is meant one or more catalysts effective to promote the in situ copolymerization of the cyanoacrylate monomer and the polymerizable compounds of the present invention, to form the copolymer product.

Suitable initiators for the purpose of the present invention are those catalysts which can be effective in situ, and which are not harmful in internal use.

N,N,dimethyl-p-toluidine (DMPT) is an exemplary catalyst being used in this invention. It is used in an amount ranging from about 0.1% to about 5% relative to the total monomers weight. Preferably, the catalyst is added in an amount of about 2%.

In another preferred embodiment taught by this invention, the polymerizable compound may be environmentally responsive, such as, among others, and without limitation, being thermo-responsive or pH-sensitive, or respond to other environmental stimuli, such as, among others, and without limitation, to ionic strength, light, electrical and/or magnetic fields, and combinations thereof. For example, monomeric acrylic acid is added to the system, thereby stabilizing the product, rendering the system with the ability to respond to pH changes. For example, PEG-PPG-PEG methacrylates and acrylates can be added to the system, rendering it, under the right conditions, to be thermo-responsive. For example, N-Isopropylacrylamide (NIPAA) (crosslinked or not), could be added to the system, rendering it, under the right conditions, to be thermo-responsive.

Since the application of the polymerizable compositions of the present invention is in biomedical applications, such as during operations, treatment of patients and other medical procedures, it is preferable to have a workable viscosity, preferably such that enables from injection to smearing and coating.

Thus, preferably, the polymerizable adhesive composition of the present invention has a viscosity which is higher than 1000 cp.

As explained hereinabove, CA adhesives suffer from a very low, difficult to use viscosity. The various solutions to address this problem have mainly been the addition of physically mixed polymers or oligomers to the CA monomer. This solution did not solve other problems, such as the undesirable mechanical properties of the obtained PCA and its extremely low biodegradability.

These problems have been successfully addressed by the inventors, who have devised a polymerizable composition which is, on one hand workable, having viscosities higher than 1000 cps, and on the other hand exhibiting acceptable adhesive and mechanical properties, as well as being able to design compositions having pre-determined biodegradability rates.

The polymerizable compounds ii of the present invention can be designed to have varying structures, properties and sizes, to provide different viscosity, as well as other properties.

However, if necessary, the polymerizable adhesive composition described herein further contains plasticizers, thickeners and other viscosity modifiers.

For example, as can be seen below, when the viscosity of the polymerizable composition was too high, additional compounds were added to the composition in varying ratios.

In particular, the inventors have used acrylate monomers selected from the group consisting of:

a) a polyether which is end-capped with one or more acrylate or methacrylate group; or b) a biodegradable oligomer composed of units having the structure of ring-opened forms of one or more cyclic esters, this oligomer being end-capped with an acrylate group.

Preferably, the acrylate monomer was used in a weight ratio of between 1:1 to 5:1 between the polymerizable compound (ii) and this acrylate monomer.

Thus, some preferred adhesive polymerizable compositions are those comprising:

a cyanoacrylate monomer; and a polymerizable compound selected from: $(HEA-828)_2$-HDI, PEG600-di-(828-MA) and PEG600-di-(8282828-MA); and Optionally comprising an acrylate monomer selected from: $HEA-LA_8$ and PEG600-dMA.

The term "828", or "$[LA]_8 [CL]_2[LA]_8$" refers to a BDG chain having 8 units of dl-lactic acid, linked to 2 units of opened ε-caprolactone, linked to another 8 units of dl-lactic acid.

The term "828-MA" refers to the "828" BDG chain, being end-capped with a methacrylate moiety.

The term "82828" or "$[LA]_8[CL]_2[LA]_8[CL]_2[LA]_8$" refers to a BDG chain having 8 units of dl-lactic acid, linked to 2 units of opened ε-caprolactone, linked to another 8 units of dl-lactic acid, linked to another 2 units of opened ε-caprolactone, linked to another 8 units of dl-lactic acid.

The term "82828-MA" refers to the "82828" BDG chain, being end-capped with a methacrylate moiety.

The term "HEA" refers to hydroxyethylacrylate.

The term "HEA-828" refers to hydroxyethylacrylate linked to a "828" BDG chain.

The term "HDI" refers to hexamethylene diisocyanate (HDI).

The term "HEA-L8" refers to hydroxyethylacrylate linked to 8 units of dl-lactic acid.

The term "PEG600" refers to polyethylene glycole having an average molecular weight of 600 grams/mole.

BRIEF DESCRIPTION OF THE DRAWINGS

Structures of additional preferable polymerizable compounds according to the present invention are shown in FIGS. 1-3.

Figure 1:
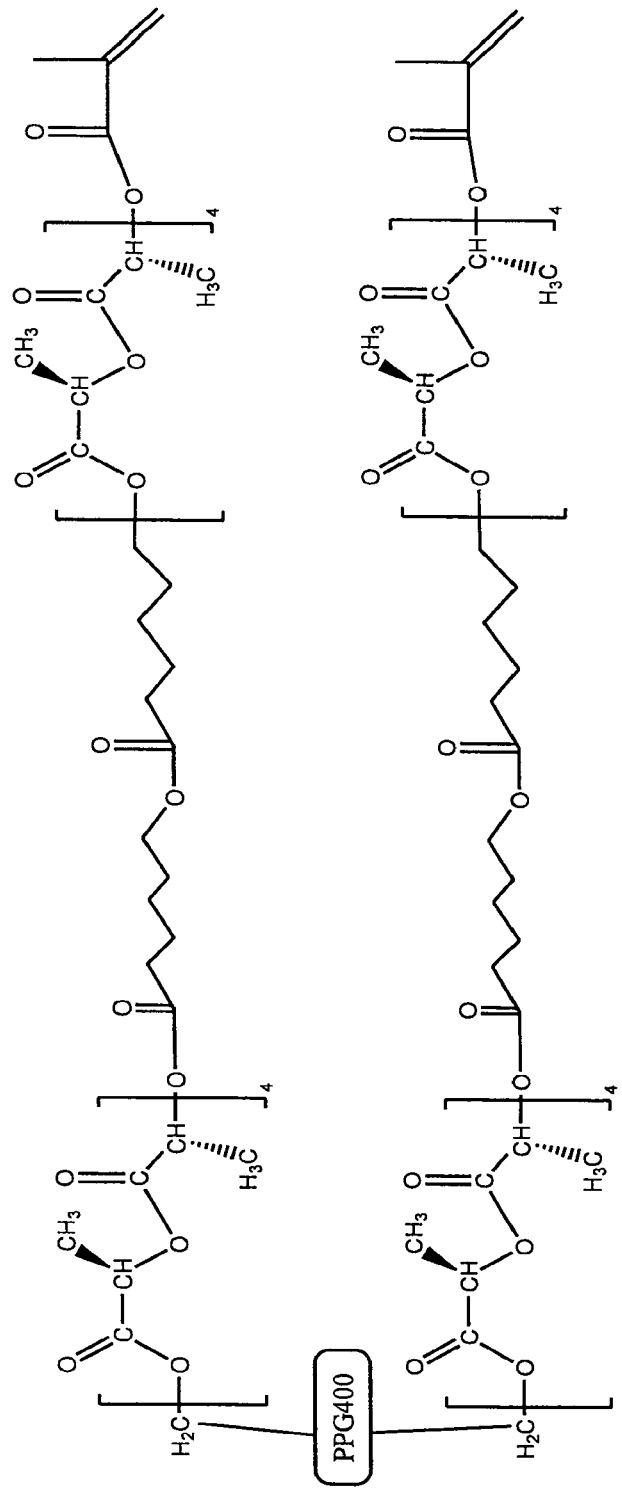
FIG. 1 shows the structure of PPG400{([LA]8[CL]2[LA]8)-MA}2.
Figure 2:
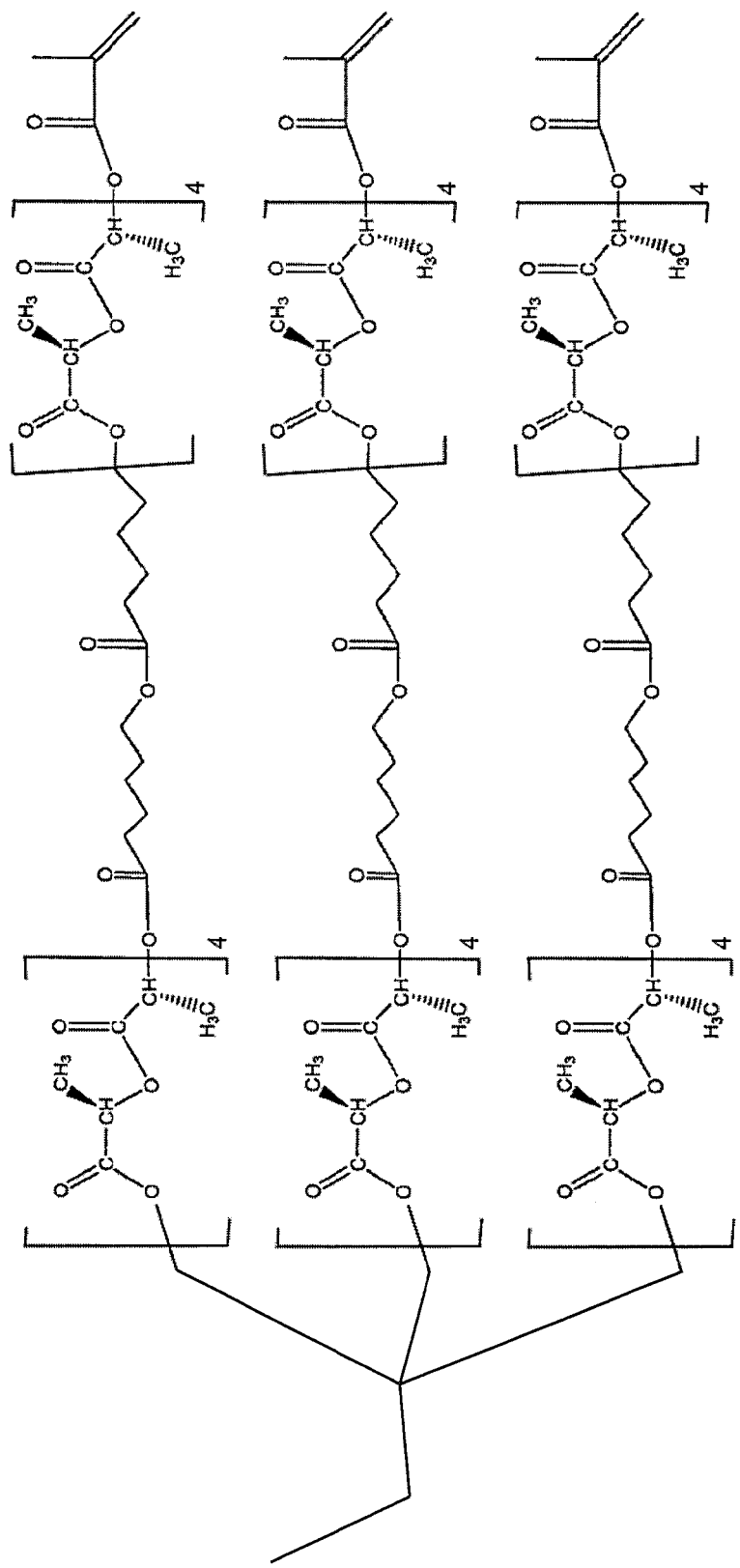
FIG. 2 shows the structure of TMP {([LA]8[CL]2[LA]8)-MA}3.
Figure 3:
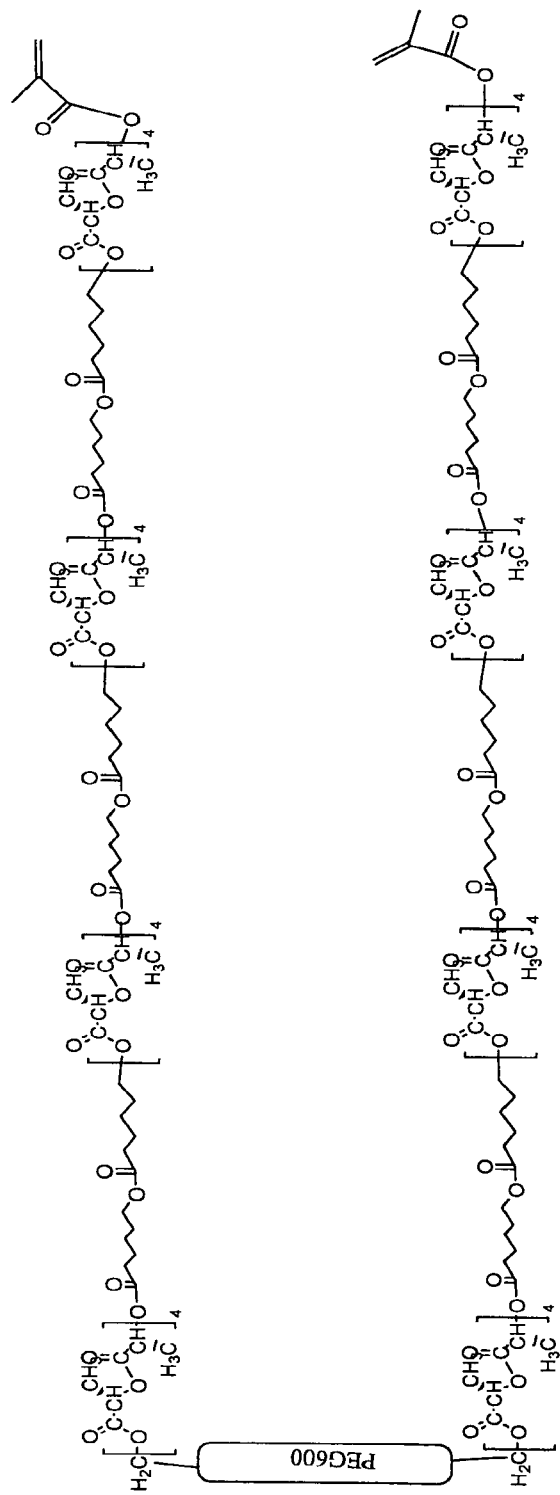
FIG. 3 shows the structure of PEG600{([LA]8[CL]2[LA]8[CL]2[LA]8[CL]2[LA]8)-MA}2.

As will be shown below, the inventors of the present invention have devised a way of forming the above-described polymerizable compounds by covalently binding at least one polymerizable C═C bond to a BDG chain or molecule, practically at any stage of their process of synthesis. For example, they could be introduced by starting from various BDG chains, optionally linked to some multifunctional moiety, and attaching thereto at least one polymerizable double bond, or—by starting from a moiety containing a polymerizable double-bond, or a chemical precursor or derivative thereof, from which a BDG chain was grown, as desired.

Thus, the polymerizable double bond(s) can be introduced into the pre-monomer compound, as it has been defined before, by a number of alternative routes to obtain the polymerizable compounds of the present invention.

I) by starting from a multifunctional moiety ═V—F containing both a polymerizable double bond(s) and an additional active group F, such as a ring opening group, in the case of lactones and similar monomers. The chain can be grown from the multifunctional moiety ═V—F, via its active group F, to obtain a desired chain length and structure, composed of a predetermined amount of monomeric units M.

Preferably, the monomeric units M are monomers of biodegradable polymers, and therefore this route leads to the formation of a chain composed of a multifunctional moiety V, containing a polymerizable C═C bond—and linked to a biodegradable chain, BDG, this chain having the general formula BDG, optionally further ending with the F functional group, as shown in Formula F1 below:

Formula F1

The multifunctional moiety =V—F is selected from compounds containing both a polymerizable carbon-carbon double bond, and an additional reactive group able to covalently bind to the BDG. Said groups can preferably be selected from hydroxyl, carboxylic acid, amine, and thiol groups or any other group able to start ring opening reactions, or able to react with other functional groups, such as acyl chlorides, isocyanates, carboxylic acids, amines, among others.

Preferably, this multifunctional moiety =V—F is an acrylate or a methacrylate as defined hereinabove.

The active group F is thus selected from hydroxyl, carboxylic acid, amine, and thiol groups or any other group able to covalently bind to the BDG, such as to start ring opening reactions. Said groups can be preferably selected from hydroxyl, carboxylic acid, amine, and thiol groups or any other group able to start ring opening reactions, or able to react with other functional groups, such as acyl chlorides, isocyanates, carboxylic acids, amines, among others.

Preferably, F is an alcohol, an amine, a carboxylic acid, a thiol etc. and from additional active groups known to start the ring open polymerization of diverse compounds, such as lactones and carbonate ring systems.

For example, the multifunctional moiety =V—F can be an acrylate, such as HEA, wherein the F groups are hydroxy groups.

The monomeric units M are selected from (dl)lactide, (l)lactide, ε-caprolactone, glycolide, dioxanone, trimethylene carbonate, among other lactones, carbonates, ortho-esters and anhydrides and combinations thereof.

The reaction between the F groups and the monomeric M units, can also be other than ring opening. For example, an hydroxyl F group may react with the COOH of lactic acid via an esterification reaction, which will continue to take place, until the required length of the chain is achieved.

Preferably, said monomeric M is a lactide or a caprolactone or combinations thereof, thereby incorporating lactoyl units and caprolactone, respectively, into the BDG chains. The obtained oligomers or polymers are polylactic acids (PLAs), polycaprolactones (PCLs) and combinations thereof, respectively.

F may also be used to bind a molecule of biological relevance, such as a drug, an oligopeptide, among many others.

Route I to obtain the polymerizable mixture of the present invention is shown in Scheme S1 below:

Scheme S1

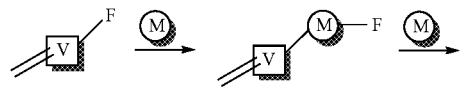

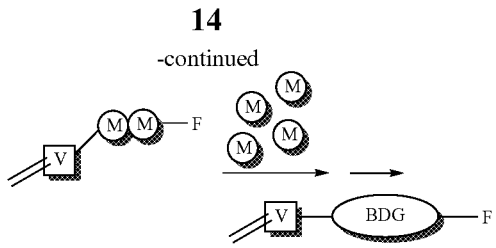

According to an exemplary process, a saturated precursor of the polymerizable compound, having the general structure MF-[BDG]$_n$ is prepared by reacting the MF moiety, for example a diol (such as PPG, PEG), a triol (such as TMP, TMPO) or having more OH groups, with a stannous 2-ethylhexanoate catalyst in a 100 ml flask, from which, prior to the reaction, air is purged and replaced by dry N$_2$. The mixture is allowed to react at 165° C., under stirring, for 120 minutes. This is followed by incorporation of ε-caprolactone (in a 10% excess) and additional (dl)-Lactide (in a 10% excess), under the same conditions, to obtain the MF-[BDG]$_n$ precursor, having a predetermined ratio of lactide (LA) and caprolactone (CL) units. Besides OH groups, MF may comprise other groups able of starting ring opening polymerization reactions, such as amine and carboxylic acid groups.

Alternatively, the reaction is repeated, being conducted at 145° C., under mechanical stirring, for 150 minutes. Furthermore, it is now found that it is possible to grow the BDG chain either in steps, namely adding the LA for the first unit, separating the product, adding the CL for the second unit, separating the product, adding the LA for the third unit etc., or—adding the complete quantities of LA and CL, whereby a random order of the LA and CL is obtained (this product is marked by "random").

This precursor is then mixed with dry chloroform and triethyleneimine in a 100 ml flask and the reaction vessel is cooled to 0° C., by immersing it in an ice bath. Then, methacryloyl chloride (in excess) is added very slowly (drop by drop, over time) and the reaction is conducted over a 24 hour period at 1200 rpm stirring to obtain the monomer end-capped on both sides with methylacrylate (MA) units.

Once the reaction is completed, as determined by GPC, most of the chloroform is evaporated under vacuum, followed by the addition of toluene and heating the solution to 80° C. for 15 about minutes. The obtained triethyleneimine HCl salt formed precipitated out of the hot toluene and is easily removed by filtration. Once all the salt had been removed, the toluene is evaporated to obtain the product as an amorphous light brown viscous liquid.

If necessary, the obtained chain can then be linked to additional chains via a conjugating agent MF to obtain a larger molecule, either symmetrical or not, linear, branched, star-shaped, or comb-shaped, which has one or more double bonds linked thereto, as shown in Formula F2 below, for a conjugating agent having a functionality of 2, and resulting in two polymerizable double bonds:

Formula F2

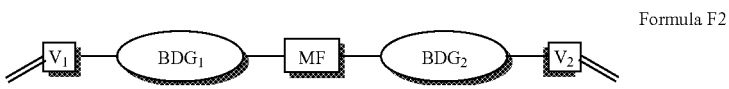

As can be seen in Formula F2, the obtained polymerizable composition has two biodegradable chains, $BDG_1$ and $BDG_2$, which are each covalently linked to a conjugating agent MF and to the multifunctional moieties $V_1$ and $V_2$, respectively.

When copolymerized with cyanoacrylate monomers, polymerizable compounds comprising more than one C=C bond, as in Formula F2, the resulting copolymer will be crosslinked.

The term "coupling agent" or "conjugating agent" refers to a substance that joins one moiety to another. The moiety may be inorganic or organic.

The conjugating agent MF is selected from the group comprising two or more moieties that can react with F, to couple two or more V monomers, such as acyl chlorides, isocyanates, carboxylic acids having a functionality of 2 of higher.

Preferably MF is a diisocyanate, such as hexamethylene diisocyanate (HDI) or a diacyl chloride, such as adipoyl chloride. MF can also be a be phosgene or a larger molecule, such as the one resulting from the reaction of a PEG chain with two HDI molecules, whereby a flexible, hydrophilic macro-diisocyanate is generated, able to react with F groups. MF may also be used to incorporate a molecule of biological relevance, such as a drug, an oligopeptide, among many others, into the system.

Generally, if MF has a functionality of n, the obtained monomer can have a multi-chain structure of n biodegradable chains BDG, each linked to a vinyl multifunctional moiety Vi, and therefore have up to n double bonds, as shown in Formula F3:

In other cases, a diol, such as PEG or PPG can be used, resulting in double-sized chains.

Obviously, it is also possible to start with an MF group having more than 2 functionalities, such as in the case of TMP or TMPO, that have 3 hydroxy groups, or citric acid or tartaric acid, or an oligomer of HEA, having x pendant OH groups, or a polyacrylic acid molecule having a MW of 2000, which has around 16 carboxylic acid groups, so it will have a functionality of 16, being able to open 16 chains.

Once the pre-desired chain length and structure are obtained, the G groups remaining at the end of these chains are reacted with a multifunctional C=C containing moiety V=, to get these chains end-capped with double bonds, as shown in Formula F2, in the case of MF having a functionality of 2:

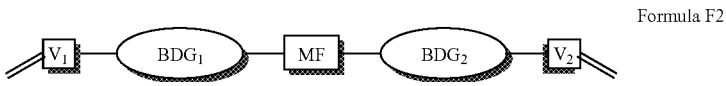

Formula F2

The multifunctional moiety MF, containing at least two active groups G, is selected from mono or poly functional alcohols, amines, carboxylic acids and thiols.

Preferably, MF is methoxyPEG, methoxyPPG, methoxyPCL, PEG, PPG, PEG/PPG block copolymers, PCL, TMP, TMPO, any dicarboxylic acid (such as adipic acid), or diamines, or dithiols, multifunctional molecules such as citric acid and tartaric acid, or malic acid, or amioacids such as glycine, alanine, aspartic acid, glutamic acid, serine, lysine, and combinations thereof.

More preferably, MF is methoxyPEG, methoxyPPG, methoxyPCL, PEG, PPG, PCL, of various molecular weights, TMP, TMPO.

In this case, the multifunctional C=C containing moiety =V—F is an acrylate or a methacrylate, such as acryloyl or methacryloyl chloride, and in general—with acryloyl and methacryloyl molecules, and also of other molecules such as acrylic acid, that in principle can react with the terminal OH of the BDG, via the esterification reaction, incorporating its C=C bond.

Route II to obtain the polymerizable compounds of the present invention is shown in Scheme S2 below (for a bifunctional MF):

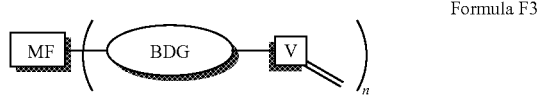

Formula F3

It should be noted that the moiety V can end with either the reactive, polymerizable double bond, or can be end-capped at the end of the reaction to deactivate one or more of these double bonds, as well known to a person skilled in the art.

Examples of compounds being prepared according to this route are presented in part A of the examples below, for the preparation of HEA-$[LA]_2$ (HEA-2), HEA-$[LA]_8$ (HEA-8), HEA-$[LA]_8$-$[CL]_2$-$[LA]_8$ (HEA-828), HEA-828-HDI-828-HEA and HEA-CL, as those have been defined hereinabove and in the examples section.

Alternatively, the monomers having the at least one double bond, can be prepared by:

II) starting from a multifunctional moiety MF, containing at least one active group G, having the same definition as those of the F functionality, as defined hereinabove, to react with the desirable monomeric units M and obtain a biodegradable chain BDG.

G groups can be, for example OH, $NH_2$, COOH and any other reactive group that can react with the reactive F group present in the C=C containing V moiety in the next stage.

For example, when MF is monofunctional, such as hexanol or methoxyPEG600, the G group is a terminal OH group, which can ring-open lactones, or react, for example, with an carboxylic acid moiety of another compound.

Scheme S2

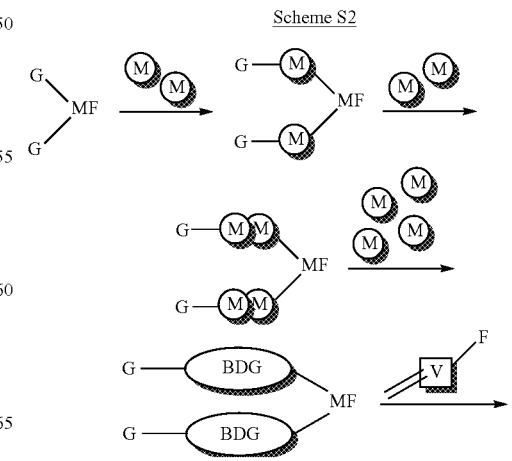

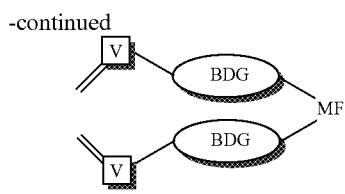

Generally, if MF has a functionality of n, the obtained polymerizable compound can have a multi-chain structure of n biodegradable chains BDG, each linked to a C=C containing moiety V, and therefore having up to n double bonds, as shown in Formula F3 below:

Formula F3

According to an exemplary process, a polymerizable compound, having the general structure V-BDG was prepared by reacting a moiety F—V=, containing at least one polymerizable double bond and at least one group that is able to start ring opening polymerization reactions or connect otherwise to the BDG component, with one or more cyclic polyesters (for example, (dl)-Lactide, ε-caprolactone etc.) and with a stannous 2-ethyl-hexanoate catalyst in a 100 ml flask, from which, prior to the reaction, air is purged and replaced by dry $N_2$. The F—V= moiety can be illustrated, for example by an hydroxyacrylate (such as hydroxyethylacrylate (HEA)), an amine-acrylate, a thiol acrylate, a carboxylic acrylate etc.

The mixture is allowed to react at 165° C., under stirring, for 120 minutes, during each addition of the cyclic polyester section, to obtain the required length and structure of the BDG chain, using a predetermined ratio of CL and LA units.

The composition of the V-BDG chains is determined by NMR analysis, by comparing several of the peaks characteristic of HEA, such as the vinyl protons at 6.2-6.4 ppm, on one hand, and peaks of the lactoyl units, such as the quartet at 5.2 ppm and the duplet appearing at 1.5-1.7 ppm, on the other hand.

In most cases, the dried V-BDG compound is then mixed with a coupling agent, such as hexamethylene diisocyanate (HDI) (in a 10% excess) and with additional stannous 2-ethyl-hexanoate catalyst in order to form a larger compound, having the general structure $MF(V-BDG)_n$. The reaction is again conducted in a 100 ml flask, from which, prior to the reaction, air is purged and replaced by dry $N_2$. The mixture is allowed to react at 85° C., under stirring, for 120 minutes. At the end of the reaction, any residual HDI is removed under vacuum.

Examples of compounds being prepared according to this route are presented in part B of the Examples section below, for the preparation of MA-PEG600-MA, MA-PCL1250-MA, MA-PCL2000-MA, MA-$[LA]_8$-$[CL]_2$-$[LA]_8$-PEG600-$[LA]_8$-$[CL]_2$-$[LA]_8$-MA (or MA-828-PEG600-828-MA), PEG600-di-(8282828-MA) and PPG400(828-MA)$_2$, as those have been defined above and in the examples section.

It should be noted, that the G groups at the end of the BDG chain(s) also enable reacting these groups (for example OH groups) with a conjugating agent, such as HDI, which can subsequently react with a HEA, HEMA, acrylic acid etc. to double or triple the chain size.

Yet, alternatively, the double-bond containing multifunctional moiety of the present invention can be prepared by:

III) starting from a multifunctional olefinic moiety, such as unsaturated dicarboxylic acids, and reacting it with a corresponding group, such as isocyanate, amine or alcohol, such that a chain will grow as the reaction proceeds Also, the dicarboxylic groups of the C=C containing moiety may be used to start ring opening reactions.

For example, the unsaturated dicarboxylic acids can be used to react with polyols, such as PEG, PPG etc. and can also be used as ring opening agents in the reaction with cyclic esters, such as lactones. Examples of lactones include, but are not limited to, lactide and ε-caprolactone, or cyclic carbonates, such as trimethylene carbonate, and similar compounds.

The term "unsaturated dicarboxylic acid" is used herein to mean a dicarboxylic acid having an unsaturated bond capable of reacting with the monomers and polymerizable compounds (polymerizable compounds) of the invention, through its double bond.

Examples of the unsaturated dicarboxylic acid used in this invention include maleic acid, fumaric acid, itaconic acid and the like.

Examples of polyhydric alcohols include, but are not limited to, ethylene glycol, diethylene glycol, propylene glycol, dipropylene glycol, 1,3-butanediol, neopentyl glycol, isopentyl glycol, 1,6-hexanediol and the like, as well as PEG, PPG, PTMG, PCL, OH-terminated PDMS.

If the monomeric units M are chosen accordingly, two or more biodegradable chains, $BDG_1$ and $BDG_2$ etc., can be obtained, being covalently linked to the unsaturated bond, thereby obtaining structure of Formula F6:

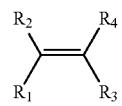

Formula F6 wherein $R_1$-$R_4$ are selected from hydrogen, C1-C16 alkyls, halogens, BDG chains, MF and a derivative of V=, as those terms have been defined hereinabove, such that at least two of $R_1$-$R_4$ are BDG groups.

For example, when $R_2$ and $R_4$ are BDG groups, a polymerizable compound of formula F7 is obtained:

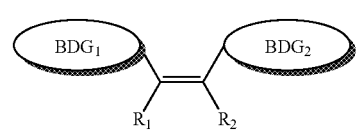

Formula F7

Route III to obtain the polymerizable compounds of the present invention is shown in Scheme S3 below, for an exemplary unsaturated dicarboxylic acid:

Scheme S3

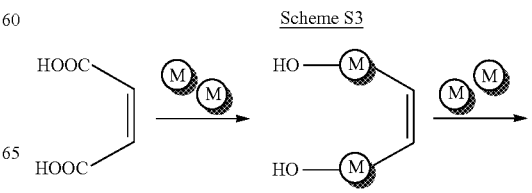

-continued

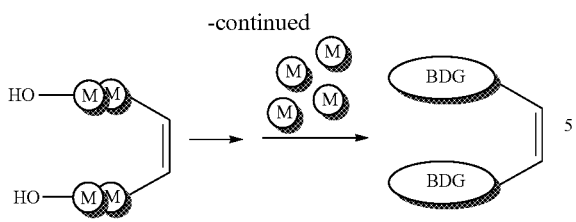

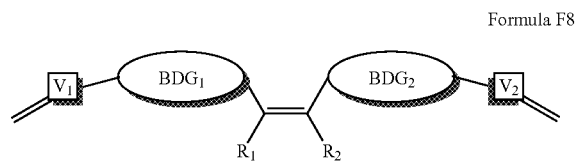

Formula F8

Alternatively, since the ring opening of cyclic esters by carboxylic acids is a slow and sometimes difficult process, it may be preferable to first link the carboxylic acids, via a coupling agent, to a multifunctional group having at least one terminal hydroxy group, such as polyols.

The modified route III to obtain the polymerizable compounds of the present invention is shown in Scheme S3 below, for an exemplary unsaturated dicarboxylic acid:

According to an exemplary such process, a polymerizable compound, having the general structure (BDG)n-MF-V is prepared by reacting a moiety V, being an unsaturated carboxylic acid (such as fumaric acid, maleic acid, itaconic acid etc.), with a biodegradable chain (BDG), optionally via a coupling agent, as follows:

A dried unsaturated carboxylic acid is mixed with (dl)-Lactide and stannous 2-ethyl-hexanoate catalyst in a 100 ml flask, from which, prior to the reaction, air is purged and replaced by dry $N_2$. The mixture is allowed to react at 165° C. under stirring, for 120 minutes. Then incorporation of the caprolactone and $[LA]_8$ segments is carried out as described hereinabove, to produce polymerizable compounds of the general formula (BDG)n-MF-V, n being the number of carboxylic acid groups within the V moiety.

Then, the COOH groups of the unsaturated carboxylic acid are reacted with the HDI coupling agent, generating the NCO capped HDI-V-HDI precursor which then reacts with an alcohol, preferably a polyol, such as PPG400, whereby the hydroxy end groups of this polyol will open the ester rings, as in the previous examples. Alternatively, the NCO capped HDI-V-HDI precursor can then also react with amine or carboxylic groups, among other groups able to react with isocyanate groups.

Examples of compounds being prepared according to this route (as well as its modified versions) are presented in part C of the examples below, for the preparation of 828-Fumaric acid-828 monomer (FA-di-(828)), 828-Maleic acid-828 monomer (MA-di-(828)), 828-itaconic acid-828 monomer (IA-di-(828)) and the fumaric acid-HDI-PPG400-di-828 monomer.

Yet another optional route to obtain the polymerizable compounds of the present invention is by:

IV) reacting a moiety V, being a substituted allyl (such as allyl isocyanate) with the end groups of the BDG chain, such that when the end groups of the BDG chain are hydroxyl, amine or thiol, or even carboxylic acids, they would be linked to the allylic compound via urethane (N—C(=O)—N}, Urea {N—C(=O)—N} or Carbamothioate {N—C(=O)—S} bonds, respectively.

It should be noted that Routes I-IV described above, can be combined in any number of ways. For example, in Route III, during the growing stage of the BDG chains, linked to the unsaturated V= group in the center of the compound, the end-groups (for example hydroxy groups) can be reacted with a double-bond containing additional multifunctional moieties V, to obtain a combination of a terminal and non-terminal double bonds in the same molecule, as shown in Formula F8:

It should be noted that the NCO group can be used at the end of the reaction of Route I, where it will react with a terminal F group (for example, an OH group) to incorporate an additional C=C into the polymerizable compounds.

Thus, route I produces a polymerizable compounds having one C=C double bond, and by introducing the allyl group, it will now have two polymerizable double bonds. In fact, the allyl NCO could be added to incorporate an additional C=C, in whatever route, by reacting with any F group.

Furthermore, it is also possible to use isopropyl triethoxy silane isocyanate (IPTS) which can react with the F groups, and incorporate into the system triethoxy silane groups. These groups will convert into silonaol in the presence of water (in vivo or in situ), and the silanol groups would then crosslink.

Preferably, the obtained polymerizable compounds of the present invention may therefore take the form of Formulas F3 and F6, or any combination thereof.

Preferably, these polymerizable compounds are chosen such that their homopolymers are biodegradable and further such that their Tg temperature, and Tm, should the homopolymer be semi-crystalline, is less than or equal to the body temperature of a person or animal, usually being below 45° C. The term homopolymers is use in this case, as indicating the BDG itself, without including the CA monomer.

The polymerizable compound, obtained by either one or more of the above-listed routes, is preferably selected from formulas F3 and F6, or any combination thereof, as defined hereinabove.

This compound is then mixed, preferably in situ, with a cyanoacrylate monomer (CA), to obtain polymerizable adhesive composition comprising a plurality of monomers.

This plurality of monomers contains at least one cyanoacrylate monomer, and at least one other monomer which has at least one polymerizable double bond.

It has now been found that the ratio between the sizes of the polymerizable compounds which form the plurality of monomers, and the number of double bonds in their structure, is an important factor in determining the suitability of the polymerizable compounds for the purposes of the present invention.

A factor, termed $F_{DK}$, describes this ratio and can be calculated, and used as one of several tools, in the prediction of the suitability of the co-polymerizable mixture, for the purposes of the present invention, as follows:

$$F_{DK} = \Sigma_j W_j * Mw_j / db_j$$

Wherein Wj is the relative weight of each monomer as part of the monomer mixture, Mwj is the molecular weight of each monomer, Dbj is the number of polymerizable double bonds in each monomer, $\Sigma_j$ is the sum of $W_j * Mw_j / db_j$ over all of the different j monomers comprising the polymer, and j is an integer $\geq 2$.

To the polymerizable mixture containing the plurality of monomers, there is also added an initiator, thereby co-polymerizing in situ the CA monomers and the C=C containing monomers. The CA and BDG monomers can be mixed ex vivo or in situ, provided that the polymerization reaction essentially takes place in situ. In fact, it is vital that the CA has to polymerize and copolymerize in contact with the tissue substrate and provide adhesiveness.

The polymerization is conducted at physiological conditions, namely at a temperature which is less than or equal to the body temperature of a person or animal, usually being below 45° C.

Additional ingredients, as discussed hereinabove, include for example benzoyl peroxide (BPO), as initiator, and dimethyl para-toluedine (DMPT), as catalyst. Both are known in in-vivo use, such the bone cement.

Considering the various applications of the polymerizable compositions described herein, these compositions may be used as part of kits, containing some or all of the components described herein.

Thus, according to a preferred embodiment of the present invention, there is provided a kit comprising any one of the polymerizable adhesive compositions described herein, wherein the at least one cyanoacrylate monomer and the at least one polymerizable compound are contained in one or more containers.

According to a preferred embodiment of the present invention, the kit further contains a means for delivering the composition to a patient.

Preferably, the means for delivering comprises a needle and a syringe. Other suitable devices include infusion devices. Additional means may also be used to facilitate delivery of highly viscous compositions, such as the use of powered devices and devices which heat the polymer composition prior to delivery.

Furthermore, there is provided a deployment device, whereby the at least one cyanoacrylate monomer and the at least one polymerizable compound are contained in the deployment device, such as a syringe, or along a deployment catheter, or at the site of performance.

One of the key considerations when engineering these adhesive compositions, is to minimize the amount of cyanoacrylate, minimizing, concomitantly, therefore, its toxicity, while displaying excellent adhesive and cohesive properties, as dictated by the specific applications of these tissue adhesives and sealants.

It has been found by the present inventors that the copolymers obtained by the above described copolymerization process retain satisfactory and controllable adhesiveness while lowering the amount of the undesirable CA monomer used in the process.

Thus, according to another aspect of the invention, there is provided the copolymerization product obtainable by the copolymerization of any one of the composition described herein.

In the present patent application, the term "copolymerization product" or "copolymer" refers to any polymer comprising at least two types of units along the polymeric backbone, which are covalently linked therebetween. This term therefore includes binary copolymers, comprising only two types of units, as well as copolymers composed of three types of units (terpolymers), and other multi-component combinations of monomers, as long as these units are linked to each other covalently and not merely physically associated.

Furthermore this term encompasses block copolymers, alternating copolymers or random copolymers, or any combinations thereof.

In particular, the terms "co-polymer" and "co-polymerization" as they are used herein, refer to the one or more polymerizable compounds of the invention, effectively being copolymerized with cyanoacrylate, under physiological conditions (in situ).

The copolymers of the present invention are formed by olefin polymerization of the CA monomer and the polymerizable compounds of the invention, which are specially designed and synthesized by the inventors to contain at least one polymerizable double bond, but which may themselves be large molecules, composed of repeating units which are covalently attached to form oligomers, polymers, co-polymers etc.

As follows from the schemes and descriptions above, it can be seen that there is now provided an adhesive copolymer composed of repeating structural units, these structural units comprising at least one SU1 unit

and at least one unit selected from SU2 and SU3:

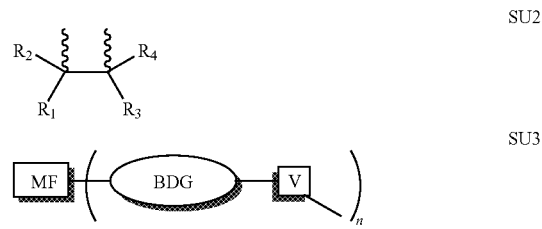

Wherein

BDG is a biodegradable chain as defined hereinabove, and preferably being composed of repeating units obtained from the ring-opening of one or more glycolide, lactide, ε-caprolactone, lactones, dioxanone and trimethylene carbonate;

V— is a group which is covalently attached to said BDG chain and is further substantially covalently attached via a carbon-carbon bond to a group selected from: the same or other BDG chain, a derivative of an V═ group or another V— group, an SU1 group, an SU2 group.

The term "covalently attached" does not exclude the existence of other levels of chemical and/or physical bonding, such as hydrophobic bonds, hydrogen-hydrogen bonds etc, in addition to the existence of pure covalent bonding.

MF, n, $R_1$, $R_2$, $R_3$ and $R_4$ are as defined hereinabove.

R is an alkyl having 1 to 16 carbon atoms.

Further preferably, the total weight of the BDG chains in these adhesive copolymers, is at least 50% wt of the total copolymer weight.

It has been found that the factor $F_{DK}$ as described above for the polymerizable composition comprising the CA monomer and the polymerizable compound ii of the invention, can also describe the size and weight ratios of the polymer, whereas the $F_{DK}$ factor can be calculated as the ratio between the measured average molecular weight of the polymer $MW_n$ and the length of its hydrocarbon backbone (n), as: $MW_n/(n/2)$.

It appears that polymers having an Fdk ratio lower than about 300 grams/mole are unsuitable as polymerizable compounds for the present copolymer system.

It may further appear that polymers having an Fdk ratio lower than about 500 grams/mole are also less suitable as polymerizable compounds for the present copolymer system.

Furthermore, the ratio between the CA units and the BDG-containing polymerizable compounds also determined a variety of properties both of the polymerizable composition and of the adhesive copolymer.

Generally, this ratio covers the 1:100 to 100:1 range. However, as it is a purpose of the present invention to lower the undesirable effects associated with high amounts of CA (toxicity, stiffness etc.), a ratio of up to 50% by weight of CA from the total weight of the monomers (CA and polymerizable compositions) is preferable. More preferably, the amount of CA will not exceed 33%, while the one or more polymerizable compounds will comprise up to 67% by weight. The amount of CA can be lowered even further, to below 20%, surprisingly resulting in co-polymers having satisfactory adhesiveness, as well as good mechanical properties, workable viscosity and an improved biodegradability ratio. Depending on the specific applications and uses of the polymerizable compositions of the present invention, the amount of CA can be lowered to about 10%, and even 5%, tailoring the adhesiveness, mechanical properties, biodegradability and additional properties of the polymer, as needed. For example, for certain uses, such as during operations, a low adhesiveness may be a requirement, in order to enable an easy detachment of a bandage at the end of the operation. For such a purpose, 5% of CA may be sufficient. For other applications, such as binding together two tissues, a stronger adhesive is required, and a 33% adhesive will prove satisfactory.

In addition, while the polyCA (PCA) is a hard and brittle polymer, causing an unpleasant sensation in the treated patient, the copolymers prepared according to the present invention have much more pleasant mechanical properties.

For example, as can be seen in the examples section below (Table I, samples D1-D8) the stiffness of the copolymers of the invention ranged from 0.8% to as much as 39%, as compared to pure PCA (considered to have 100% stiffness).

Therefore, according to a preferred embodiment of the present invention, there is provided an adhesive copolymer as described herein, wherein the stiffness thereof is lower than 33%, 20%, 10%, 5% and even less than 1% compared to the stiffness of ethyl 2-cyanoacrylate at physiological conditions.

In addition, as can also be seen in the examples section below (Table I, samples D1-D8) the adhesiveness of the copolymers of the invention ranged from 14% to no more than 38% as compared to the adhesiveness of pure PCA, while using no more than 33% wt of the CA monomer. The adhesiveness can be lowered even further, without having an undesirable effect on the mechanical or other properties of the product, if so desired, depending on the application.

Therefore, according to another preferred embodiment of the present invention, there is provided an adhesive copolymer as described herein, wherein the adhesiveness thereof, to a biomaterial substrate at physiological conditions, is lower than 50%, 40%, 30%, 20% and even less than 10% compared to the stiffness of ethyl 2-cyanoacrylate at physiological conditions.

Thus, it has been found that the adhesive copolymer described herein can be characterized by one or more of the following properties:
a) an adhesiveness to a biomaterial substrate ranging from 5% to about 50% compared to the adhesiveness of ethyl 2-cyanoacrylate at physiological conditions;
b) a stiffness which is lower than 50% compared to the stiffness of ethyl 2-cyanoacrylate at physiological conditions;
c) an $F_{DK}$ value $\geq -500$ grams/mole, wherein $F_{DK}=MW_n/(n/2)$.

In addition, while the polyCA (PCA), shown in Scheme S4-I, is slowly degrading polymer, practically being termed "non-degradable", substituting some of the CA units in its backbone by polymerizable compounds having one or more double bonds, enables incorporating biodegradable chains (represented as springs in the Scheme S4 II) within the polymer backbone. When these BDG chains degrade, it results in cleavage of the chains and breaking up of the copolymer structure (see Scheme S4-III, the absence of the springs reflects their biodegradation).

As noted hereinabove, the copolymer of the present invention already has smaller amounts of CA units, as compared to the same weight of PCA, and introducing polymerizable compounds having BDG chains with 2 or more double bonds, increases this effect by enabling the further breaking up of these PCA blocks.

Scheme S4

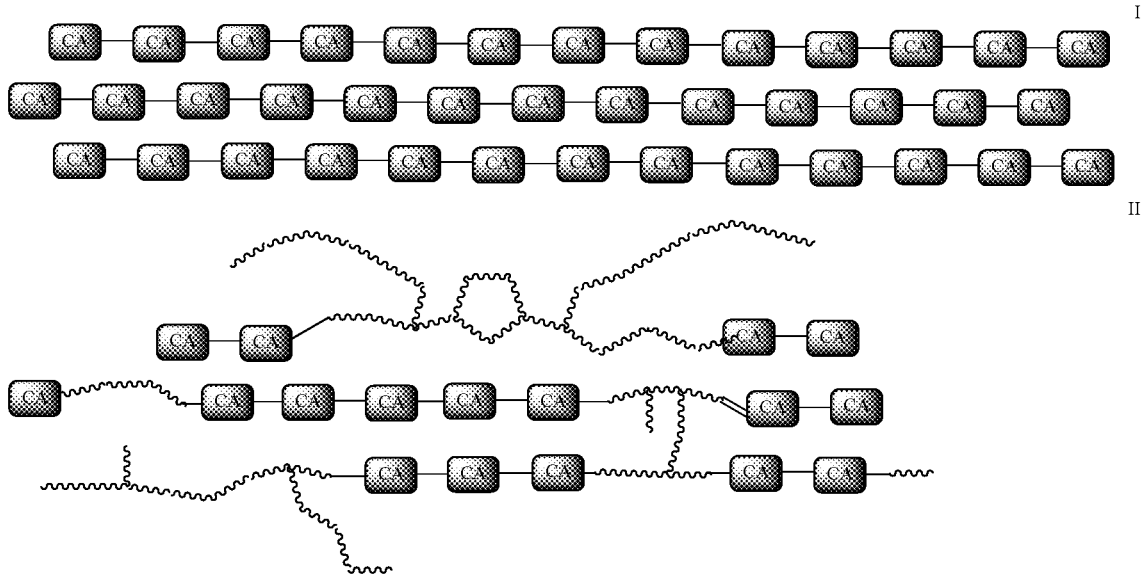

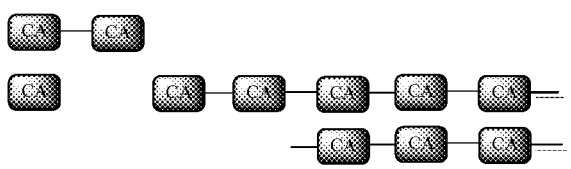
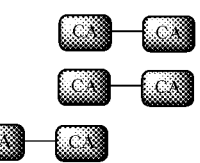

III

As can be understood from Scheme 4, the degradability of BDG chains forming part of physical mixtures of PCAs and BDG chains, will result in a system similar to I in Scheme 4, whereas the degradability of BDG chains forming part of the covalently-bound copolymers of the present invention, results in a system similar to III in Scheme 4, which is a clear advantage, as explained hereinabove.

Thus, according to a preferred embodiment of the present invention, there is provided the adhesive copolymer described herein, being a substantially mono-component copolymer.

Furthermore, according to a preferred embodiment of the present invention, there is provided the adhesive copolymer described herein, being substantially free of a PCA homopolymer.

The term "substantially free of a PCA homopoymer" as defined herein refers to a polymeric system where PCA homopolymer represent only a small fragment (up to 20% wt) of the total mass polymerized.

Furthermore, the adhesive copolymer described herein remains substantially free of a PCA copolymer after being kept at physiological conditions for 14 days.

The biodegradability of the obtained copolymer is therefore also an important factor in designing the polymerizable composition, including choosing the type and quantity of polymerizable compound(s). Thus, the requirement from the polymerizable compositions to have an $F_{DK}$ factor which is higher than 250 grams/mole, should be combined with a requirement of having less than 50% wt CA, as explained hereinabove, and should preferably further be combined with a requirement that the adhesive copolymer of the present invention will have a biodegradability rate which is higher than that of pure PCA.

Naturally, the required biodegradability rate will be determined according to the specific uses, and will vary accordingly.

Therefore, according to a preferred embodiment of the present invention, there is provided an adhesive copolymer as described herein, having a pre-determined degradability rate.

Yet another advantage of using the polymerizable compounds of the present invention is that these polymerizable compounds, when having more than one double bond, can further act as a biodegradable crosslinking agent, which may form links between chains, later breaking these bonds up, to change the mechanical and physical properties of the polymer, as the copolymer degrades.

Therefore, according to a preferred embodiment of the present invention, there is provided the adhesive copolymer described herein, being a crosslinked copolymer.

Furthermore, according to another preferred embodiment of the present invention, the V= moiety, or any component thereof, is a crosslinking agent of the crosslinkable polymerizable composition.

Given the properties described above for the copolymers of the invention, the polymerizable compositions of the invention are most suitable for biomedical applications, in particular as tissue adhesives and sealants to be used in the human or animal body.

Thus, according to another aspect of the invention, there is provided the use of the polymerizable adhesive composition described herein as a tissue adhesive, sealant, or blocking agent.

When used in the biomedical field, the working temperature (Tw) of the polymerizable compositions of the present invention is about body temperature (Tb).

The term "animal" refers to warm-blooded animals and, in particular, to mammals and human beings.

The term "body temperature" therefore refers to a temperature lower than 50° C., preferably lower than 45° C., and more preferably to a temperature which is in the range of 35° C.-42° C., in the case of humans.

Since the copolymers of the present invention have relatively small amounts of CA units, it is only negligibly toxic, thus significantly increasing its scope of use, as compared to presently known CA products.

In particular, it can be used internally, in contrast to commercial CA-based bioadhesives, which are indicated for topical use only.

Thus, according to a preferred embodiment of the present invention, there is provided the use described herein, being a topical use or an internal use.

Another advantage of the present polymerizable compounds is that they can be polymerized in situ.

Thus, according another aspect of the invention, there is provided the process of preparing the adhesive copolymer described herein, this process comprising the in situ polymerization of the polymerizable adhesive compositions described herein.

The present invention further concerns articles of manufacture composed of the polymerizable compositions of the present invention, being composed of cyanoacrylate monomers and non-cyanoacrylate polymerizable compounds.

These articles of manufacture may include:

1. Articles, such as bandages, films, meshes, fabrics, ribbons, sponges and non-woven structures, having at least one layer of a cyanoacrylate monomer and at least one layer of a polymerizable compound, having at least one polymerizable double bond, and a biodegradable chain BDG, preferably having a plurality of such layers; and 2. Articles, such as bandages, films, mashes, fabrics, ribbons, sponges and non-woven structures, having at least one zone of a cyanoacrylate monomer and at least one zone of a polymerizable compound, having at least one polymerizable double bond, and a biodegradable chain BDG, preferably having a plurality of such layers.

The term "layer", as used herein, refers to an adhesive layer, this being one or more regions of an adhesive polymerizable composition that has been formulated or processed so as to be substantially solid, coherent, and non-flowable. The adhesive layer may comprise a single continuous region or it may comprise a plurality of discontinuous regions or layers.

The layer may comprise one or more of the component of the compositions taught by this invention.

The term "zone", is used interchangeably with the term "region" or "adhesive region", thereby including various areas of adhesive, whether continuous or disconnected, that have similar properties, such as adhesiveness, biodegradability etc.

Thus, the final product may be homogeneous in space or may consist of different zones displaying different properties, these zones being able to be nanometric, up to macroscopic, continuous or discontinuous, creating independent or interconnected domains within the system, having several geometries, architectures and spatial arrays, dispersed homogeneously or heterogeneously, isotropically or anisotropically.

The term "substantially solid", as used herein, refers to an adhesive composition or layer that is in a solid or semi-solid condition. In one aspect, a "substantially solid" adhesive composition or layer can be characterized as a continuous or cohesive mass that does not readily flow or separate when subjected to gravitational forces and which cannot be readily expressed through a syringe outlet or other similarly-sized opening or orifice. Thus, the term "substantially solid" excludes runny adhesive liquids, viscous adhesive liquids, and even thick adhesive gels that are able to flow when subjected to gravity and/or which can be readily expressed through a syringe outlet or other similarly-sized opening or orifice. The term "substantially solid", when used in the context of an adhesive composition or layer, also excludes dry particulate adhesive compositions or powders. One characteristic of the "substantially solid" adhesive compositions or layers for biological applications, is that they become more adhesive when the exposed surface is moistened with, e.g., saliva, water or any aqueous medium, thereby turning into a sticky material that is able to more strongly adhere to the bodily surface, compared to a substantially solid adhesive composition or layer that has not been moistened. The adhesive composition at the surface may become a viscous liquid, paste or gel, at least temporarily, depending on the amount of moisture that is applied to the surface of the "substantially solid" adhesive composition or layer.

In both of these cases, given the properties and high reactivity of the CA monomer, these articles of manufacture need to be hermetically packaged to prevent exposure to humidity, and hence premature polymerization.

The article of manufacture would be opened on site, for example at the Operating Room, at the very last moment, and then attached to the surface being treated.

The term "surface" as used herein is a biological surface, which is any surface on or within an animal or human organism. Examples of "biological surfaces" to which the polymerizable compositions of the present invention may be applied include any epithelial surface such as the skin, respiratory tract, gastrointestinal tract and genitourinary tract.

An exemplary use for such articles of manufacture can be to seal numerous small air leaks on the surface of the lungs. The substrate onto which the adhesive composition comprising the CA monomer and/or of the polymerizable compound (containing the BDG chain and the polymerizable double bond) can be either stable or degradable. When only one component only is present on the surface of the substrate, the second component may be added at the last moment, prior to use. For example, the polymerizable compound may be present at the surface of an appropriate substrate, coated on the surface, physically entrapped or bound, covalently or otherwise, and the CA component will be added at the last minute, prior to use. Furthermore, stabilizers can be added onto that surface to have acceptable shelf life and the catalytic system would be added at the last moment. Besides being supplied in an appropriate sealed packaging that will ensure satisfactory shelf life, the surface of the product of manufacture may also be covered to further protect it from air and the surgeon would peel that cover off when he is ready to use it.

The adhesiveness of these articles of manufacture would be either a strong adherence or a weak temporary one, depending on the medical need. Additional, once component can be on the surface of the substrate, while the second component may be in a separate region of the substrate. For example, surface versus bulk. Only upon use, both components are brought together on the surface that is going to be adhered.

In another embodiment, these articles of manufacture disclosed hereby comprise also an additional solid component or components that can appear in a diversity of shapes, sizes and geometries, including, without limitation, spheres, particles of any other shape, capsules, fibers, ribbons, films, meshes, fabrics, non-woven structures, foams, porous structures of different types, each of them having the possibility of being solid, porous, hollow and/or combinations thereof. These solid component or components may be solid already at deployment time or they may be generated in situ, during or immediately after deployment or later on, over time. The solid component or components may differ significantly in their behavior and in their different properties, including, without limitation, their composition as well as their physical, rheological, mechanical and biological characteristics.

In yet another embodiment, the articles of manufacture disclosed hereby comprise also an additional liquid component or components, wherein said liquid component or components may differ significantly in their behavior and in their different properties, including, without limitation, their composition as well as their physical, rheological, mechanical and biological characteristics.

Also, the two components may be embedded into the substrate, in ultra-dry acidic conditions, avoiding any polymerization and/or degradation.

Also, the BDG may be physically entrapped on the surface of the substrate (films, sponge etc.) while the CA would be "stored", in an efficiently stabilized manner in the bulk of the substrate. Upon use, the CA in the bulk is squeezed into the surface where it polymerizes and copolymerizes and performs as an adhesive. This could occur only on one side of the substrate or on both sides, or all sides for any other geometry. Also, the CA "stored" can be stabilized in the bulk of the substrate, while the BDG is covalently bound to the surface of the substrate.

Also, the substrate can be nano, micro or macroscopic particles. They could also be introduced in a void, for example, and then react together via the composition disclosed hereby.

However, it should be noted that the adhesive copolymer disclosed hereby can also be applied in a diversity of non-biomedical applications.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Analytical Methods

All the biodegradable components were kept dry or were dried at 120° C. under vacuum and stirring. The synthesis was performed in the molten state (without solvents) under $N_2$ atmosphere and mechanical stirring, although it can also be performed in solution, if needed.

The preparation of some pre-monomers of the invention is described in D. Cohn & G. Lando: "*Tailoring lactide/caprolactone co-oligomers as tissue adhesives*", Biomaterials 25 (2004) 5875-5884.

The commercial cyanoacrylate tissue adhesives used were Dermabond (Ethicon, USA), Hystoacryl (B. Braun, Germany) and Loctite's non-biomedical "Super Glue" product.

Ethylene glycol (EG) was obtained from Baker.

(l)-Lactide (marked as l-LA) and (dl)-Lactide (marked as LA) were obtained from Boehringer Ingelheim, Germany.

N,N-dimethyl-p-toluedine (DMPT) catalyst was purchased from Acros.

All other chemicals were purchased from Sigma-Aldrich and were used without further purification steps.

LA stands for lactic acid.
CL stands for ε-caprolactone.
PCL stands for polycaprolactone.
NA stands for not available.
MA stands for methylacrylate.
828 stands for $[LA]_8[CL]_2[LA]_8$
82828 stands for $[LA]_8[CL]_2[LA]_8[CL]_2[LA]_8$
PEG600 is a polyethylene glycol having an average Mw of 600 grams/mol. PEG1000 is a polyethylene glycol having an average Mw of 1000 grams/mol.

PPG400 is a polyproplylene glycol having an average Mw of 400 grams/mol. PPG2000 is a polyproplylene glycol having an average Mw of 2000 grams/mol.

TMPO stands for ethoxylated trimethylolpropane;
TMP stands for trymethylol propane;
NMR spectra were recorded on a Bruker 400 MHz instrument with chemical shifts reported in ppm relative to the residual deuterated solvent or the tetramethylsilane internal standard.

Viscosity was measured using a Haake Rheometer.

Mechanical Properties were measured using an Instron 4502 machine.

The adhesiveness of the different copolymers was determined in vitro using a meat substrate and the following model: A polypropylene (PP) net (3×3 cm²) was adhered to the substrate using the copolymerizable system of the present invention (comprising the CA monomer and the biodegradable polymerizable compounds). The area of adhesion was 3×3 cm². The CA monomer, the biodegradable polymerizable compounds, and benzoyl peroxide were mixed and then N,N-dimethyl-p-toluidine was added to effect a copolymerization reaction. After 15 minutes at 37° C., the PP net was pulled at a rate of 10 cm/minute and the force required for failure was measured.

GPC analysis was performed on a Waters 2690 apparatus with a Waters 410 detector.

Biodegradation was determined by immersing the polymer in an aqueous medium at 37° C.

The exothermic effect of polymerization was measured using a thermocouple embedded within the mass of the polymerizing material.

Swelling was determined by immersing the sample in an aqueous medium and weighing the sample periodically.

Part A: Preparation of Polymerizable Compounds by Route I

General Procedure (for BDG Composed of LA and CL Units)

A saturated precursor of the polymerizable compound, having the general structure MF-[BDG]$_n$ was prepared by reacting the MF moiety, for example a diol (PPG, PEG) or triol (TMP, TMPO) with (dl)-Lactide (in a 10% excess) and with a stannous 2-ethyl-hexanoate catalyst in a 100 ml flask, from which, prior to the reaction, air was purged and replaced by dry $N_2$. The mixture was allowed to react at 165° C., under stirring, for 120 minutes. This was followed by incorporation of ε-caprolactone (in a 10% excess) and additional (dl)-Lactide (in a 10% excess), under the same conditions, to obtain the MF-[BDG]$_n$ precursor, having a predetermined ratio of lactide (LA) and caprolactone (CL) units.

The quantities used to prepare precursors according to this route are summarized below:

| MF | Quantity MF | n | BDG | Quantity (dl)-Lactide | Quantity CL | catalyst | Viscosity (Pa·s) yield | Tg ° C. |
|---|---|---|---|---|---|---|---|---|
| PEG600 | 5.00 (1.14 mmoles) | 2 | $[LA]_8[CL]_2[LA]_8$ | 30.2 grams (209.86 mmoles) | 1.81 grams (15.9 mmoles) | 0.0084 grams (0.021 mmoles) | 3.265 86% yield | 0 |
| PPG400 | 0.80 grams (2.00 mmoles) | 2 | $[LA]_8[CL]_2[LA]_8$ | 5.07 grams (35.2 mmoles) | 1.00 grams (8.8 mmoles) | 5.07 grams (35.2 mmoles) | 12.6 90% yield | NA |

Alternatively, the reaction was repeated, being conducted at 145° C., under mechanical stirring, for 150 minutes. Furthermore, it was now found that it is possible to grow the BDG chain either in steps, namely adding the LA for the first unit, separating the product, adding the CL for the second unit, separating the product, adding the LA for the third unit etc., or—adding the complete quantities of LA and CL, whereby a random order of the LA and CL is obtained (this product is marked by "random").

Precursors prepared according to this modification are summarized below:

| MF | Quantity MF | n | BDG | Quantity (dl)-Lactide | Quantity CL | catalyst | Product | Tg °C. |
|---|---|---|---|---|---|---|---|---|
| PPG2000 | 18.00 grams, 9.00 mmoles | 2 | $[LA]_{30}$ | 42.80 grams, 297 mmoles | none | 0.28 grams, 0.69 mmol | a white Viscous | −4 |
| TMPO | 9.00 grams | 3 | $[LA]_{14}$ | 28.18 grams | none | 0.20 0.5 mmoles | semi- solid | −5 |
| TMP | 4.70 grams, 35.03 mmoles | 3 | $[LA]_8$-$[CL]_2$- $[LA]_8$-$[CL]_2$- $[LA]_8$ | 63.57 gr. 23.79 14.89 gr. | 9.87 gr. 6.15 gr. | 0.44 gr. 0.09 gr. 0.16 gr. 0.05 gr. 0.1 gr. | | −5 |
| TMP (random) | 0.50 grams, 3.73 mmoles | 3 | $[LA]_{24}$-$[CL]_4$ | 20.16 grams | 5.57 grams, 48.80 mmoles | 0.20 0.5 mmoles | | 6 |

This precursor was then mixed with dry chloroform and triethyleneimine in a 100 ml flask and the reaction vessel was cooled to 0° C., by immersing it in an ice bath. Then, methacryloyl chloride (in excess) was added very slowly (drop by drop, over time) and the reaction was conducted over a 24 hour period at 1200 rpm stirring to obtain the polymerizable compound end-capped on both sides with methylacrylate (MA) units.

Once the reaction was completed, as determined by GPC, most of the chloroform was evaporated under vacuum, followed by the addition of toluene and heating the solution to 80° C. for 15 about minutes. The obtained triethyleneamine HCl salt formed precipitated out of the hot toluene and was easily removed by filtration. Once all the salt had been removed, the toluene was evaporated to obtain the product as an amorphous light brown viscous liquid.

Quantities used for the preparation of the MA-828-PEG600-828-MA polymerizable compound were:
Precursor (828-PEG600-828): 20.00 grams, 5.92 moles;
Chloroform: 30 ml, 197 mM;
Triethyleneamine TEA: 3.60 grams, 3.57 mmole;
Methacryloyl chloride: 3.72 grams, 3.57 mmol;
The product appeared as an amorphous light brown viscous liquid, obtained in a 94% yield.

Similar quantities were used starting from the 8282828-PEG600-8282828 and 828-PPG400-828 precursors.

Thus, the polymerizable compounds prepared according to this route (Route I) are summarized below:

| MF | n | BDG | V= | Viscosity Pa·s | Tg °C. |
|---|---|---|---|---|---|
| PEG600 | 2 | $(LA)_8(CL)_2(LA)_8$ | MA | 3.265 | 0 |
| PPG400 | 2 | $(LA)_8(CL)_2(LA)_8$ | MA | 12.6 | NA |
| PPG400 | 2 | $(LA)_8(CL)_2(LA)_8(CL)_2(LA)_8$ | MA | 14.2 | 5 |
| PPG2000 | 2 | $(LA)_{30}$ | NY | NA | NA |
| TMPO | 3 | $(LA)_{14}$ | NY | NA | NA |
| TMP | 3 | $(LA)_8(CL)_2(LA)_8(CL)_2(LA)_8$ | NY | NA | NA |

NY = not yet synthesized.

As a comparison, another compound was prepared, starting from 14 l-lactic acid (l-LA) units and PPG1000, to obtain a more slowly degradable compound.

Another compound prepared according to this route, but which does not contain a BDG chain, and hence was not used on its own in subsequent polymerization reactions, was PEG600(MA)$_2$. This compound was used in combination with the polymerizable compounds of the invention, aiming at fine-tuning the viscosity of the copolymerizable composition, as well as tailoring the average molecular weight between crosslink junctions and the flexibility and hydrophilicity of the product.

As another comparison, two additional compounds were prepared starting from commercial hydroxy-terminated poly-caprolactones: PCL1250 and PCL 2000. They were reacted with methacryloyl chloride, as described above to produce bi-functional MA-capped caprolactone chains: MA-PCL1250-MA and MA-PCL2000-MA, using the following quantities:

For the Preparation of MA-PCL1250-MA:
Poly-caprolactone 1250 (PCL1250): 10.00 grams, 8.00 mmoles;
dry chloroform: 30 ml, 266.66 mM;
triethyleneimine (TEA): 3.24 grams, 32 mmole;
methacryloyl chloride: 3.35 grams, 32 mmoles (in excess);
The MA-PCL1250-MA product (11.51 grams, 7.2 mmoles, 90% yield) appeared as a light brown waxy solid.

For the Preparation of MA-PCL2000-MA:
The same process was repeated, starting from the PCL2000 (10 grams, 5 mmoles) to obtain the MA-PCL2000-MA product (8.56 grams, 4 mmoles, 80% yield) as a brown waxy solid.

The MA-PCL1250-MA and MA-PCL2000-MA were not used in subsequent tissue adhesive experiments, due to the slow degradability of the PCL chains, and may be used in other applications which require especially slow biodegradability, such as in bone repair.

Part B: Preparation of Polymerizable Compounds by Route II

General Procedure (for BDG Composed of LA and CL Units)

A polymerizable compound, having the general structure V-BDG was prepared by reacting a moiety V═, containing at least one polymerizable double bond and at least one group that is able to start ring opening polymerization reactions or connect otherwise to the BDG component. This can be illustrated, for example by an acrylate substituted b a reactive F group, such as hydroxyethylacrylate (HEA), with one or more cyclic polyesters (for example, (dl)-Lactide, ε-caprolactone etc.) and with a stannous 2-ethyl-hexanoate catalyst in a 100 ml flask, from which, prior to the reaction, air was purged and replaced by dry N$_2$. The mixture was allowed to react at 165° C., under stirring, for 120 minutes, during each addition of the cyclic polyester section, to obtain the required length and structure of the BDG chain, using a predetermined ratio of CL and LA units.

The composition of the ═V-BDG chains was determined by NMR analysis, by comparing several of the peaks characteristic of HEA, such as the vinyl protons at 6.2-6.4 ppm, on one hand, and peaks of the lactoyl units, such as the quartet at 5.2 ppm and the duplet appearing at 1.5-1.7 ppm, on the other hand.

The quantities used to prepare precursors according to this route are summarized below:

For the Preparation of HEA-[LA]$_8$:
Hydroxyethylacrylate (HEA): 5.00 grams, 43.1 mmoles;
(dl)-lactide: 27.33 grams, 189.8 mmoles, 10% excess;
Stannous 2-ethyl-hexanoate catalyst: 0.35 grams, 0.86 mmoles.

The HEA[LA]$_8$ product was a light brown, amorphous, viscous liquid, and was left under vacuum to remove the excess lactone. The product displays a glass transition at around −10° C. The viscosity of HEA-[LA]$_8$ was determined to be around 15 Pascal seconds (Pa·s) (15,000 cp). Due to its low viscosity it was used in later experiments to decrease the viscosity of larger polymerizable compounds, which had very high viscosities. This product was used to prepare the larger HEA-[LA]$_8$[CL]$_2$[LA]$_8$ compound (see below).

For the preparation of HEA-[LA]$_8$[CL]$_2$[LA]$_8$:
Dried HEA-[LA]$_8$: 5.00 grams, 7.2 mmoles;
ε-caprolactone: 1.81 grams, 15.9 mmoles, 10% excess;
Stannous 2-ethyl-hexanoate catalyst (first stage): 0.02 grams, 0.005 mmoles);
(dl)-lactide: 27.33 grams, 189.8 mmoles, 10% excess;
Stannous 2-ethyl-hexanoate catalyst (second stage): 0.35 grams, 0.86 mmoles;

The product displayed a glass transition at around −3° C. and a viscosity of about 570 Pa·s (570,000 cp) exhibiting the consistency of a light wax.

These relatively short-chained compounds, having one double chain per chain (n=1), were not used in subsequent polymerization experiments on their own, but rather as part of polymerizable mixtures.

Furthermore, another short-chained compound, having one double chain per chain (n=1), HEA-[CL]$_2$ was prepared, as described hereinabove, but was not used in subsequent experiments due to its very slow degradability and undesirable mechanical properties.

In most cases, the dried V-BDG compound was then mixed with a coupling agent, such as hexamethylene diisocyanate (HDI) (in a 10% excess) and with additional stannous 2-ethyl-hexanoate catalyst in order to form a larger compound, having the general structure MF(V-BDG)$_n$. The reaction was again conducted in a 100 ml flask, from which, prior to the reaction, air was purged and replaced by dry N$_2$. The mixture was allowed to react at 85° C., under stirring, for 120 minutes. At the end of the reaction, any residual HDI was removed under vacuum.

The quantities used to prepare polymerizable compounds, coupled by HDI, appear below:
For the Preparation of HEA-828-HDI-828-HEA:
Dried HEA-([LA]$_8$-[CL]$_2$-[LA]$_8$): 5.00 grams, 3.3 mmoles;
Hexamethylene diisocyanate (HDI): 0.31 grams, 1.84 mmoles, 10% excess;
Stannous 2-ethyl-hexanoate catalyst: 0.002 grams, 0.005 mmoles;

The product (5.0 grams, 47% yield) exhibited the consistency of a heavy waxy material, and its viscosity was determined to be around 1,880 Pa·s (1,880,000 cp).

HEA-828-HDI-828-HEA Mixtures

For subsequent experiments, the two compounds (HEA-828-HDI-828-HEA) and HEA-8, prepared as described hereinabove, were mixed to produce a mixture of 50 wt % HEA-8 and 50 wt % (HEA-828-HDI-828-HEA). Its viscosity was 535 Pa·s.

Furthermore, the two compounds (HEA-828-HDI-828-HEA) and (MA-PEG600-MA), prepared as described hereinabove, were also mixed in two ratios:

a) 25% MA-PEG600-MA: 75% (HEA-828-HDI-828-HEA); and
b) 50% MA-PEG600-MA: 50% (HEA-828-HDI-828-HEA)

The viscosity of mixture (a) was only 5% of that of (HEA-828-HDI-828-HEA) alone. The adhesive strength it attained was 13% of that of the 100% commercially available cyanoacrylate adhesive (ethyl cyanoacrylate, Superglue).

The viscosity of mixture (b) was below 2% of that of (HEA-828-HDI-828-HEA) alone. The stiffness was only 3% of that of the 100% cyanoacrylate adhesive (ethyl cyanoacrylate, Superglue).

Part C: Preparation of Polymerizable Compounds by Route III

General Procedure (for BDG Composed of LA and CL Units):

A polymerizable compound, having the general structure (BDG)n-MF-V was prepared by reacting a moiety V=, being an unsaturated carboxylic acid (such as fumaric acid, maleic acid, itaconic acid etc.), with a biodegradable chain (BDG), optionally via a coupling agent, as follows:

A dried unsaturated carboxylic acid is mixed with (dl)-Lactide and stannous 2-ethyl-hexanoate catalyst in a 100 ml flask, from which, prior to the reaction, air is purged and replaced by dry N$_2$. The mixture is allowed to react at 165° C. under stirring, for 120 minutes. Then incorporation of the caprolactone and [LA]$_8$ segments is carried out as described hereinabove, to produce polymerizable compounds of the general formula (BDG)n-MF-V, n being the number of carboxylic acid groups within the V moiety.

The ring opening of cyclic esters by carboxylic acids is a slow and difficult reaction, and therefore in most cases it was found preferable to link the BDG chain to the unsaturated carboxylic acids via a coupling agent, such as HDI and a multifunctional moiety MF.

In this case, the COOH groups of the unsaturated carboxylic acid (V=) are first reacted with HDI, generating the NCO capped HDI-V-HDI precursor which then react with an alcohol, preferably a polyol, such as PPG400, whereby the hydroxy end groups of this polyol will open the ester rings, as in the previous examples.

For example, Fumaric acid-di-(HDI-PPG400-828) was prepared as follows:

[I] Preparation of the OCN-Capped HDI-Fumaric Acid-HDI:

Dried fumaric acid (2 grams, 17.23 mmoles), hexamethylene diisocyanate (HDI, 6.35 grams, 37.9 mmoles, 10% excess) and stannous 2-ethyl-hexanoate catalyst (0.002 grams, 0.2 mmoles) were introduced into a 100 ml flask, from which, prior to the reaction, air was purged and replaced by dry N$_2$.

The mixture was allowed to react at 65° C., under stirring, for 120 minutes. During the reaction CO$_2$ bubbles could be observed, due to the reaction between the NCO and COOH groups, whereby amide moieties were generated. At the end of the reaction, the residual HDI was removed under vacuum. Yield was 80% (6.24 grams).

[II] Preparation of the HO-Terminated PPG400-HDI-Fumaric Acid-HDI-PPG400

Dried OCN-capped HDI-fumaric acid-HDI (6.24 grams, 13.78 mmoles) was reacted with PPG400 (12.13 grams, 30.32 mmoles, 10% excess) and stannous 2-ethyl-hexanoate catalyst (0.16 grams, 0.4 mmoles). Prior to the reaction, air was purged and replaced by dry $N_2$. The mixture was allowed to react at 65° C., under stirring, for 120 minutes and the yield was 85% (14.67 grams).

[III] Preparation of ([LA]$_8$-[CL]$_2$-[LA]$_8$)-PPG400-HDI-Fumaric Acid-HDI-PPG400-([LA]$_8$-[CL]$_2$-[LA]$_8$) (828-PPG400-HDI-FA-HDI-PPG400-828)

The process described hereinabove was repeated, starting from dried PPG400-HDI-fumaric acid-HDI-PPG400 (2.5 grams, 2 mmoles) and using the following quantities: (dl)-Lactide (5.07 grams, 35.2 mmoles, 10% excess), stannous 2-ethyl-hexanoate catalyst (0.04 grams, 0.1 mmoles), ε-caprolactone (1.00 grams, 8.8 mmoles, 10% excess). The yield of the product was 70% (5.62 grams).

Additional terminal double bonds may be attached as described in part A.

Part D: Preparation of Polymerizable Compounds by Route IV

General Procedure (for BDG Composed of LA and CL Units)

A polymerizable compound of the invention can be prepared by reacting a moiety V, being a substituted allyl (such as allyl isocyanate) with the end groups of the BDG chain, such that when the end groups of the BDG chain are carboxylic, hydroxyl, amine or thiol, they would be linked to the allylic compound via urethane (N—C(=O)—N), Urea {N—C(=O)—N} or Carbamothioate {N—C(=O)—S} bonds, respectively.

Part E: Reaction of the Polymerizable Compounds with Cyanoacrylates Monomers Under Physiological Conditions to Obtain the Bioadhesives of the Present Invention

General Procedure

The polymerization was conducted on a meat substrate (or in a vial), using the following model:

A polypropylene (PP) net (5×5 cm$^2$) was adhered to the substrate using the copolymerizable compounds of the present invention, at pre-determined weight ratios of a commercial ethyl 2-cyanoacrylate (CA) monomer and one or more polymerizable compounds, containing one or more double bonds, as presented in Table 1 below.

The area of adhesion was 3×3 cm$^2$. The mixture of CA monomer and the polymerizable compound(s) was further mixed with a benzoyl peroxide initiator (2%) mixed and was smeared on the net. Then, a N,N-dimethyl-p-toluedine (DMPT) catalyst (2%) was added and smeared along with the mixture from previous step to effect a free radical copolymerization reaction and obtain a homogeneous layer of adhesive. Alternatively, all of the components were mixed homogeneously and then smeared on the substrate surface. The polymerization was conducted at 37° C. or higher (for example, at 100° C.).

For each polymer, the adhesiveness (as % of 100% commercial PCA) and stiffness (MPa) were measured after 15 minutes from time of application. Then the % stiffness was calculated in comparison to PCA's stiffness (taken as 100%).

The degradation of the polymers G' (KPa) was measured at 0, 2, 6, 11, 14 days. Then the % degradation was calculated in comparison to the first day's G' (taken as 100%).

Furthermore, a factor ($F_{DK}$) indicating the size of the hydrocarbon backbone of the polymer, determined by the number of double bonds in the polymerization system and the sizes of the substituents on the hydrocarbon chain, was calculated according to Formula I below and is presented in Table I:

$$F_{DK} = \Sigma_j W_j * Mw_j / db_j$$

Wherein Wj is the relative weight of each monomer or polymerizable compound, as part of the monomer mixture, Mwj is the molecular weight of each monomer, Dbj is the number of polymerizable double bonds in each monomer, $\Sigma_j$ is the sum of $W_j * Mw_j / db_j$ over all of the different j monomers comprising the polymer, and j is an integer ≥2.

Alternatively, the $F_{DK}$ factor can be calculated as the ratio between the measured average molecular weight of the polymer $MW_n$ and the length of its hydrocarbon backbone (n), as: $MW_n/(n/2)$.

As can be seen from Table I, polymer samples having $F_{DK}$ values higher than about 500 grams/(mole double bond) had good adhesion as compared to the control PCA, yet had better mechanical properties (lower stiffness) compared to it.

However, this in itself was insufficient to guarantee biodegradability or satisfactory mechanical and/or adhesive properties, as can be seen from comparative samples D9-D14 in Table II, representing the combinations of CA with the HEA-CL$_2$ PCL1250-dA and PCL2000-dA compounds, which did not degrade at all in 14 days at physiological conditions.

TABLE I

| Sample | % wt CA monomer | % wt telechelic oligomer | Telechelic oligomer | Adhesiveness (as % of 100% PCA) | Calculated $F_{DK}$ (grams/mole double bond) | Stiffness (as % of 100% PCA) | Degradation (wt loss in % from day 0) at 2, 6, 11, 14 days |
|---|---|---|---|---|---|---|---|
| D1 | 15% | 85% | 50% HEA-LA8 50% (HEA-828)$_2$-HDI | 26% | 640.6 | 20.7 | 23.6%, 63.6% |
| D2 | 33% | 67% |  | 34% | 789.8 | 25.8 | 69.6%, 72.2% |
| D3 | 15% | 85% | 25% PEG600-dMA 75% (HEA-8-2-8)$_2$-HDI | 25% | 1080.9 | 0.8 | 23%, 30%, 63%, 70% |
| D4 | 33% | 67% |  | 37% | 878.5 | 6.6 | 26%, 30%, 70%, 77% |
| D5 | 15% | 85% | 50% PEG600-dMA 50% (HEA-8-2-8)$_2$-HDI | 14% | 832.0 | 31.3 | −28%, 9%, 37%, 50% |
| D6 | 33% | 67% |  | 29% | 682.3 | 19.1 | 33.9%, 36.4%, 42.6%, 46.3% |
| D7 | 15% | 85% | PEG600-di-(828-MA) | 24% | 1506.9 | 39.1 | 29%, 37%, 43%, 54%, 66% |
| D8 | 33% | 67% | PEG600-di-(8282828-MA) | 38% | 2292.9 | 1.2 | 4%, 87.5%, 92% |

TABLE II

Comparative Examples

| Sample | % wt CA monomer | % wt Other monomer(s) | Other monomer(s) | Adhesiveness (as % of 100% PCA) | Calculated $F_{DK}$ (grams/mole double bond) | Stiffness (as % of 100% PCA) | Degradation (wt loss in % from day 0) at 2, 6, 11, 14 days |
|---|---|---|---|---|---|---|---|
| control | 100% | 0% | — | 100% | 125 | 100% | 0%, 0%, 0%, 0% |
| D9 | 15% | 85% | HEA-CL2 (Bisomer) | 15% | 239.8 | No data | 0%, 0%, 0%, 0% |
| D10 | 33% | 67% | | 20% | 215.5 | No data | 0%, 0%, 0%, 0% |
| D11 | 15% | 85% | PCL1250-dA | 39% | 626.6 | 46.9 | 0%, 0%, 0%, 0% |
| D12 | 33% | 67% | | 62% | 520.4 | 66.4 | 0%, 0%, 0%, 0% |
| D13 | 15% | 85% | PCL2000-dA | 30% | 945.3 | 82.0 | 0%, 0%, 0%, 0% |
| D14 | 33% | 67% | | 82% | 771.6 | 89.8 | 0%, 0%, 0%, 0% |

The invention claimed is:

1. A polymerizable adhesive composition comprising:
(i) at least one cyanoacrylate monomer;
(ii) at least one polymerizable compound containing (a) two or more polymerizable carbon-carbon double bonds and (b) one or more biodegradable (BDG) chains; and
(iii) a polymerization initiator and a polymerization catalyst, such that said initiator and said catalyst are effective in situ, wherein
the polymerizable compound is selected from: (HEA-828)$_2$-HDI, PEG600-di-(828-MA) and PEG600-di-(8282828-MA); and
further optionally comprising an acrylate monomer selected from: HEA-LA8 and PEG600-dMA.

2. A polymerizable bioadhesive composition comprising:
(i) at least one cyanoacrylate monomer; and
(ii) two or more biodegradable (BDG) chains each terminated with an end group containing a polymerizable carbon-carbon double bond, wherein said two or more BDG chains are linked to a single multifunctional moiety;
said polymerizable bioadhesive composition further comprising a free radical polymerization initiator and a polymerization catalyst, such that said initiator and said catalyst are effective in situ;
further wherein said composition contains from 10% to 33% of said cyanoacrylate monomer(s) from the total weight of said polymerizable composition.

3. The polymerizable adhesive composition of claim 2, wherein the compound (ii) is represented by the formula F3,

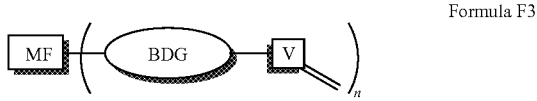

Formula F3

Wherein:
a) BDG is a biodegradable chain composed of repeating units obtained from the ring-opening of one or more glycolide, lactide, c-caprolactone, lactones, dioxanone and tri methylene carbonate;
b) V= is an end group covalently attached to the BDG chain, said V=providing the polymerizable carbon-carbon double bond;
c) MF is linked to n BDG chains via n groups, each of the groups being independently selected from water, hydroxyl, amine, thiol, aldehyde, isocyanate (NCO), acyl chloride, carboxylic acid-terminated segments, amines, thiols, alcohols, a molecule containing a reactive unsaturated bond, wherein the BDG chain may be the same or different;
d) n is an integer between 2 and 20.

4. The polymerizable adhesive composition of claim 3, wherein said MF is linked to said n BDG chains via at least one bond selected from the group consisting of ester bonds, amide bonds, thioester bonds, urea bonds and urethane bonds.

5. The polymerizable adhesive composition of claim 4, wherein at least one of the groups is a diol or triol group, and wherein said MF is linked to said n BDG chains and via at least one an ester bond.

6. The polymerizable adhesive composition of claim 5, wherein said diol is polyethylene glycol (PEG) or polypropylene glycol (PPG).

7. The polymerizable adhesive composition of claim 5, wherein said triol is trimethylolpropane or ethoxylated trimethylolpropane.

8. The polymerizable adhesive composition of claim 4, wherein MF is a diisocyanate linked to said BDG chains via an urethane bond.

9. The polymerizable adhesive composition of claim 8, wherein said diisocyanate is hexamethylene diisocyanate (HDI).

10. The polymerizable adhesive composition of claim 2, wherein the BDG chain is composed of repeating units obtained from ring-opening polymerization of lactide and of c-caprolactone.

11. The polymerizable adhesive composition of claim 10, wherein said V= is an acrylate group or a methacrylate group.

12. The polymerizable adhesive composition of claim 2, having a viscosity higher than 1000 cp.

13. The polymerizable adhesive composition of claim 2, wherein said cyanoacrylate monomer is selected from the group consisting of alkyl 2-cyanoacrylate, alkenyl 2-cyanoacrylate, alkoxyalkyl 2-cyanoacrylate, and carbalkoxyalkyl 2-cyanoacrylate, wherein the alkyl group of said one or more cyanoacrylates has 1 to 16 carbon atoms.

14. The polymerizable adhesive composition of claim 2, further containing an inhibitor of anionic and/or radical polymerization.

15. The polymerizable adhesive composition according to claim 2, which further comprises (iii) an acrylate monomer or a methacrylate monomer selected from the group consisting of:
a) a polyether which is end-capped with one or more acrylate groups or methacrylate groups; and
b) a biodegradable oligomer composed of units having the structure of ring-opened forms of one or more cyclic esters, said oligomer being end-capped with an acrylate group or a methacrylate group.

16. A polymerizable bioadhesive composition according to claim 2, wherein said composition contains from 15 to 33% of said cyanoacrylate monomer(s) from the total weight of said polymerizable composition.

17. A polymerizable bioadhesive composition according to claim 2, wherein the free radical polymerization initiator is selected from the group consisting of benzoyl peroxide, dicumyl peroxide, methyl ester ketone peroxide and lauryl peroxide.

18. A process for preparing tissue adhesive, comprising the in situ polymerization of the polymerizable bioadhesive composition of claim 2.

\* \* \* \* \*